(12) United States Patent
Urban

(10) Patent No.: US 6,326,495 B2
(45) Date of Patent: *Dec. 4, 2001

(54) PROCESS FOR PREPARING 8-CYCLOPENTYL-6-ETHYL-3-[SUBSTITUTED]-5,8-DIHYDRO-4H-1,2,3A,7,8-PENTAAZA-AS-INDACENES AND INTERMEDIATES USEFUL THEREIN

(75) Inventor: Frank J. Urban, Waterford, CT (US)

(73) Assignee: Pfizer Inc., New York, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/516,549

(22) Filed: Mar. 1, 2000

Related U.S. Application Data

(60) Provisional application No. 60/131,949, filed on Apr. 30, 1999.

(51) Int. Cl.[7] .................. C07D 487/14; C07D 471/04

(52) U.S. Cl. ........................... 546/82; 546/119

(58) Field of Search ................ 546/82, 119

(56) References Cited

FOREIGN PATENT DOCUMENTS

| 9501980 | 1/1995 | (WO) | .............. | C07D/471/04 |
|---|---|---|---|---|
| 9612720 | 5/1996 | (WO) | .............. | C07D/471/04 |
| 9639408 | 12/1996 | (WO) | .............. | C07D/471/14 |

OTHER PUBLICATIONS

E. W. Sutherland, et al., Pharmacol. Rev., 12, pp. 265–299 (1960).
J. A. Beavo, et al., TIPS, 11, pp. 150–155 (1990).
C. D. Nicholson, et al., TIPS, 12, pp. 19–27 (1991).
M. W. Verghese, et al., J. Mol. Cell Cardiol., 12 (Supp. II), S 61, (1989).
T. J. Torphy, "Directions for New Anti–Asthma Drugs", eds. S. R. O'Donnell and C. G. A. Persson, 1988, pp. 37–53, Birkhauser–Verlag.
W. Friers, FEBS Letters, 285, pp. 199–212 (1991).
C. E. Spooner, et al., Clinical Immunology and Immunopathology, 62, pp. S11–S17 (1992).

*Primary Examiner*—Bernard Dentz

(57) ABSTRACT

The invention concerns a method of preparing an 8-cyclopentyl-6-ethyl-3-[substituted]-5,8-dihydro-4H-1,2, 3a,7,8-pentaaza-as-indacene compound of the formula:

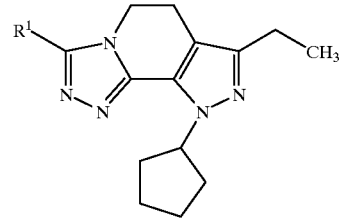

and pharmaceutically acceptable salt forms thereof, where $R^1$ is hydrogen; alkyl; alkoxy; alkoxyalkyl; alkenyl; cycloalkyl; cycloalkylalkyl; a saturated or unsaturated heterocyclic-$(CH_2)_n$—group; or a group of the formula —$(Y)_b$—$(Z)_c$-phenyl-$(R^5)_a$; comprising: (a) subjecting a solventless reaction mixture of γ-caprolactone and p-methoxybenzylamine to heating whereby there is produced an amide compound N-protected by p-methoxybenzyl; (b) reducing said amide compound whereby there is produced an amino alcohol compound N-protected by p-methoxybenzyl; (c) acylating said aminoalcohol compound with ethyl oxalyl chloride whereby there is produced an oxalamic acid ethyl ester compound N-protected by p-methoxybenzyl; (d) oxidizing said oxalamic acid ethyl ester compound whereby there is produced an oxalamide ketone compound N-protected by p-methoxybenzyl, of the formula:

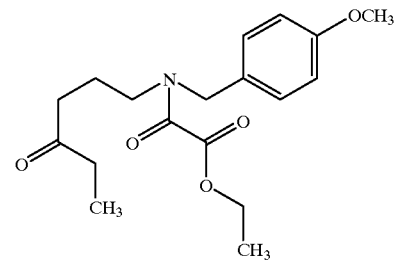

(e) ring closing said oxalamide ketone compound whereby there is produced a pyridinone compound N-protected by p-methoxybenzyl, of the formula:

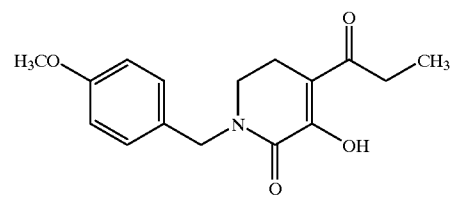

(f) O-methylating said pyridinone compound whereby there is produced a 3-methoxy-pyridinone compound N-protected by p-methoxybenzyl; (g) treating said 3-methoxy-pyridinone compound with cyclopentylhydrazine, whereby there is produced a pyrazolopyridinone compound N-protected by p-methoxybenzyl; (h) deprotecting said pyrazolopyridinone compound by removing said p-methoxybenzyl group therefrom, whereby there is produced a lactam compound of the formula:

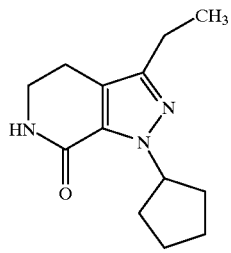

(i) esterifying said lactam compound whereby there is produced a corresponding imino ester (imidate) compound of the formula:

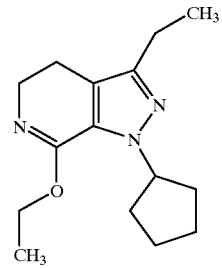

and (j) treating said imino ester (imidate) compound with a carboxylic hydrazide compound of the formula: $R^1$—C(=O)—NH—NH$_2$, where $R^1$ has the same meaning as set out further above; whereby there is produced said 8-cyclopentyl-6-ethyl-3-[substituted]-5,8-dihydro-4H-1,2,3a,7,8-pentaaza-as-indacene.

9 Claims, No Drawings

PROCESS FOR PREPARING 8-CYCLOPENTYL-6-ETHYL-3-[SUBSTITUTED]-5,8-DIHYDRO-4H-1,2,3A,7,8-PENTAAZA-AS-INDACENES AND INTERMEDIATES USEFUL THEREIN

REFERENCE TO APPLICATIONS

This application claims benefit of No. 60/131,949 filed Apr. 30, 1999.

Reference is made to application Ser. No. 08/973,590 filed Jun. 6, 1995 now U.S. Pat. No. 6,004,974, published as WO 96/39408 on Dec. 12, 1996, which discloses tricyclic 5,6-dihydro-9H-pyrazolo[3,4-c]-1,2,4-triazolo[4,3-a] pyridines having biological activity as inhibitors of phosphodiesterase type IV (PDE4) and the production of tumor necrosis factor (TNF), useful in the treatment of asthma, bronchitis, chronic obstructive pulmonary disease, allergic rhinitis, psoriasis, dermatitis, rheumatoid arthritis, and other inflammatory, allergic and immunological diseases and conditions. Several processes for preparing said tricyclic compounds are described therein, but nothing that is disclosed would teach the person of ordinary skill the improved process of the present invention.

BACKGROUND OF THE INVENTION

The class of compounds prepared in accordance with the present invention have been named herein as 8-cyclopentyl-6-ethyl-3-[substituted]-5,8-dihydro-4H-1,2,3a,7,8-pentaaza-as-indacenes, although this class of compounds has been referred to in the art as being tricyclic 5,6-dihydro-9H-pyrazolo[3,4-c]-1,2,4-triazolo[4,3-a]pyridines. In whatever preferred manner said class of compounds is named, however, the compounds prepared in accordance with the process of the present invention are represented by the following Formula (1.0.0):

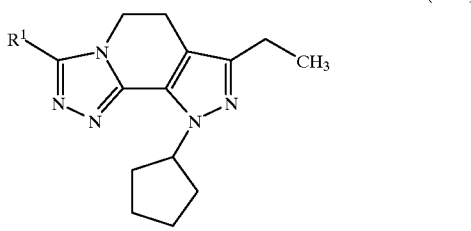

(1.0.0)

where $R^1$ is a member selected from the group consisting of hydrogen; $(C_1-C_6)$ alkyl; $(C_1-C_4)$ alkoxy; $(C_1-C_4)$ alkoxy $(C_1-C_4)$ alkyl; $(C_2-C_8)$ alkenyl; $(C_3-C_7)$ cycloalkyl and 1'-methyl thereof, $(C_3-C_7)$ cycloalkyl$(C_1-C_2)$ alkyl; a saturated or unsaturated $(C_4-C_7)$ heterocyclic-$(CH_2)_m$—group where m is 0, 1, or 2, comprising one or two heteroatoms selected from O, S, S(=O)$_2$, N, NR$^3$, O and N or NR$^3$, S or S(=O)$_2$ and N or NR$^3$, and N or N$^3$ and N or NR$^3$, where $R^3$ is hydrogen or $(C_1-C_4)$ alkyl; and a group of Formula (1.1.0):

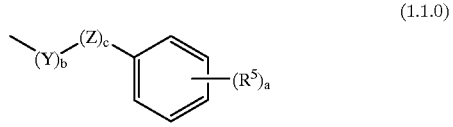

(1.1.0)

where a is 1–5, and b and c are 0 or 1; $R^5$ is hydrogen, hydroxy, $(C_1-C_4)$ alkyl, $(C_2-C_4)$ alkenyl, $(C_1-C_4)$ alkoxy, $(C_3-C_6)$ cycloalkoxy, halogen, trifluoromethyl, $CO_2R^{3a}$, $CONR^{3a}R^{3b}$, $NR^{3a}R^{3b}$, $NO_2$, or $SO_2NR^{3a}R^{3b}$; where $R^{3a}$ and $R^{3b}$ are independently hydrogen or $(C_1-C_4)$ alkyl; Z is O, S, S(=O)$_2$, C(=O), or NR$^3$; and Y is —$(C_1-C_4)$ alkylene- or —$(C_2-C_4)$ alkenylene-, either of which is optionally mono-substituted by hydroxy; wherein each above-recited alkyl, alkenyl, cycloalkyl, alkoxyalkyl or heterocyclic group is substituted by 0 to 3 substituents selected from $(C_1-C_2)$ alkyl, trifluoromethyl, and halogen.

The above-described pentaaza-as-indacenes are known compounds having biological activity as inhibitors of phosphodiesterase type IV (PDE4) and the production of tumor necrosis factor (TNF). That biological activity makes said pentaaza-as-indacenes useful in the treatment of various inflammatory, allergic and immunological diseases and conditions, which include asthma, bronchitis, chronic obstructive pulmonary disease, allergic rhinitis, psoriasis, dermatitis, and rheumatoid arthritis. The above-mentioned therapeutic utilities of said pentaaza-as-indacenes are well established and accepted in the art, as shown, e.g., by the published application WO 96/39408 already noted further above. The use of inhibitors of PDE4 and TNF in the treatment of inflammatory, allergic and immunological diseases and conditions is also well known in the art. See, e.g., WO 95101980 published on Jan. 19, 1995, and WO 96/12720 published on May 2, 1996.

A preparation process for 8-cyclopentyl-6-ethyl-3-[substituted]-5,8-dihydro-4H -1,2,3a,7,8-pentaaza-as-indacenes which is known in the art and described in above-mentioned published application WO 96/39408, uses a p-methoxyphenyl N-protecting group in the initial stages of the synthesis. The overall preparation process, depicted for the species where $R^1$ is 2-thienyl, is represented by reaction Scheme 1 set out further below.

In step a of the overall synthesis, 2-pyrrolidinone and 4-iodoanisole are heated in the presence of copper powder and potassium carbonate to give the N-(4-methoxyphenyl) pyrrolidin-2-one, which in step b is treated with ethylmagnesium bromide Grignard reagent to give an aliphatic ketone after ring opening of the pyrrolidinone. This ketone is isolated and then undergoes ring closure to form the 3-hydroxy-1,2,5,6-tetrahydropyridin-2-one intermediate in steps c and d using ethyl oxalyl chloride and sodium hydroxide in step c and sodium ethoxide and ethanol in step d. The corresponding 3-methoxy intermediate is obtained in step e by treatment with 3-methyl-p-tolyltriazine, after which in step f the 4,5,6,7-tetrahydro-7-oxo-1H-pyrazolo[3,4-c]pyridine intermediate is obtained by ring closure using cyclopentyl hydrazine hydrochloride. The 4-methoxyphenyl N-protecting group is removed in step g by treatment with cerium (IV) ammonium nitrate to give the lactam intermediate, after which in step h the lactam intermediate is converted to the corresponding thiolactam intermediate by treatment with phosphorus pentasulfide. The tricyclic final product is prepared in steps i', j and k by treatment with anhydrous hydrazine in step i, followed by treatment with 2-thiophene carbonyl chloride in step j and refluxing in step k.

SCHEME 1

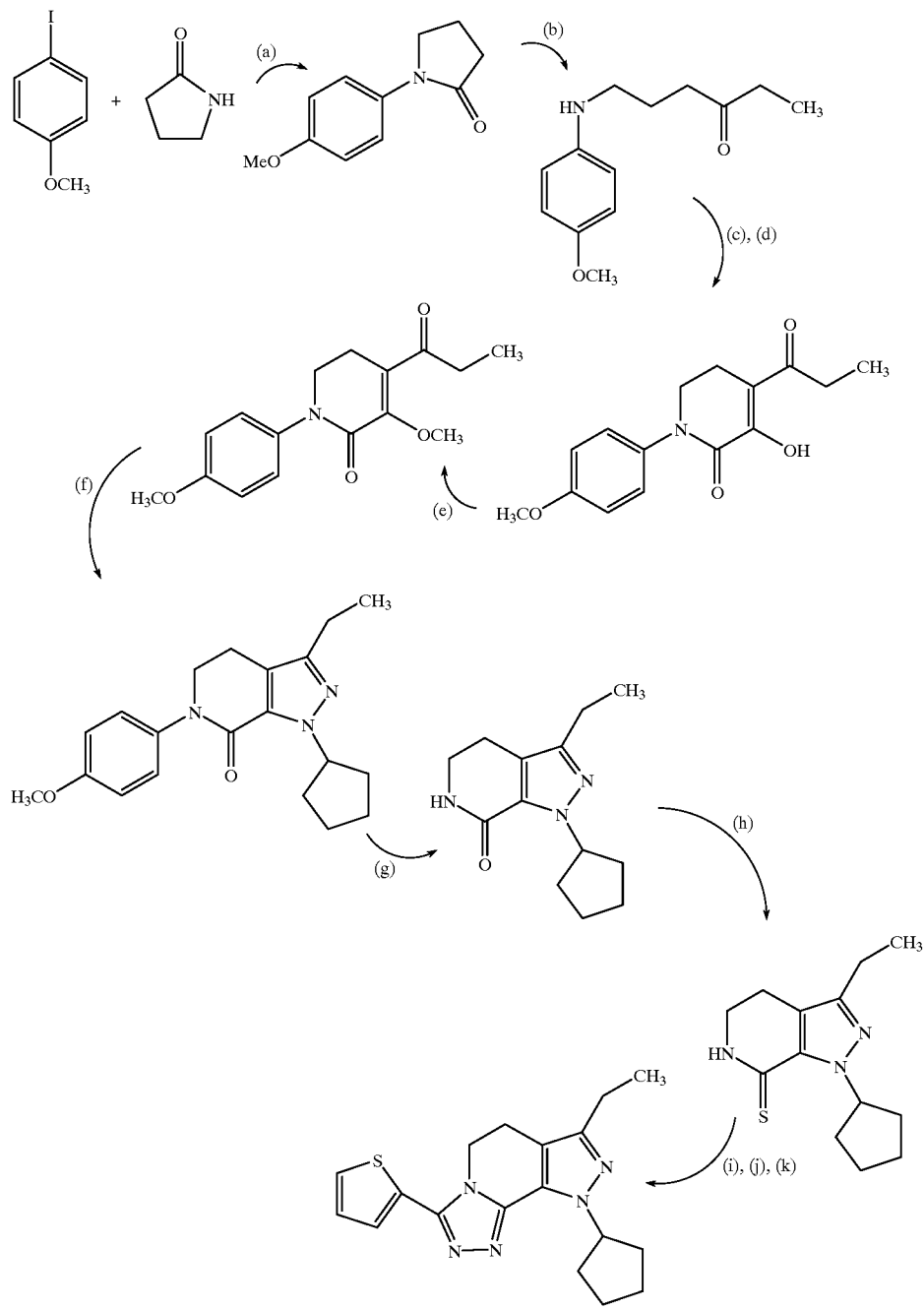

The above-described method of the prior art suffers from a number of disadvantages, however. Step a for example, is a neat reaction carried out in the presence of copper powder and potassium carbonate at a temperature of about 150° C. When carried out at a scale larger than that used for exploratory synthesis, the reaction of step a becomes exothermic and may form an intractable solid mass upon cooling unless the solvent, e.g., ethyl acetate, is added immediately to the crude melt comprising the reaction mixture. Further, in step e the cost of the triazine reactant, 3-methyl-p-tolyltriazine, is sufficiently high that it creates a problem with the overall economics of the process in Scheme 1, especially when considered in light of the fact that the yields in virtually all of the steps in the process of Scheme 1 are sub-optimal.

Moreover, in step b the aliphatic ketone prepared with the aid of the Grignard reagent, ethylmagnesium bromide, may be carried out in ethyl ether with substantially no problems, but in tetrahydrofuran, a much less problematic solvent, there is a tendency for side reactions to take place, leading to side products and potential stability problems. The p-methoxyphenyl protected amino ketone prepared in step b may be sufficiently unstable that it cannot be stored. Other problems may arise with regard to the synthesis and purification of the cyclopentyl hydrazine reactant; and the ceric ammonium nitrate deprotection of the p-methoxyphenyl amide.

Still further problems may be encountered with the procedures entailed in the use of thiolactam chemistry to introduce the triazole component of the tricyclic nucleus of the final products. These include the use of anhydrous hydrazine when introducing the triazole ring with thienoyl chloride. Anhydrous hydrazine is a hazardous chemical substance, fuming in air, and capable of exploding during distillation if traces of air are present. Accordingly, there is a currently unfilled need in the art for a process of preparing 8-cyclopentyl-6-ethyl-3-[substituted]-5,8-dihydro-4H-1,2,3a,7,8-pentaaza-as-indacenes which is less problematic, is more facile, and has greater economic feasibility. Responsive to that need, the process of preparation of the present invention is presented in detail herein.

DESCRIPTION OF THE STATE OF THE ART

The present invention is in the field of methods used for synthetic preparation of 8-cyclopentyl-6-ethyl-3-[substituted]-5,8-dihydro-4H-1,2,3a,7,8-pentaaza-as-indacenes, which are known compounds which possess biological activity as selective inhibitors of phosphodiesterase (PDE) type IV and the production of tumor necrosis factor (TNF). Consequently, the process of the present invention have direct beneficial utility in providing the art with an improved method for obtaining compounds which are in turn known to be useful in the treatment of asthma, arthritis, bronchitis, chronic obstructive airway disease, psoriasis, allergic rhinitis, dermatitis, and other inflammatory diseases, AIDS, septic shock and other diseases in mammals, especially humans.

Since the recognition that cyclic adenosine phosphate (AMP) is an intracellular second messenger, e.g., in E. W. Sutherland, and T. W. Rall, *Pharmacol. Rev.*, 12, 265, (1960), inhibition of the phosphodiesterases has been a target for modulation and, accordingly, therapeutic intervention in a range of disease processes. More recently, distinct classes of PDE have been recognized, e.g., in J. A. Beavo et al., *TiPS*, 11, 150, (1990), and their selective inhibition has led to improved drug therapy. See, e.g., C. D. Nicholson, M. S. Hahid, *TiPS*, 12, 19, (1991). More particularly, it has been recognized that inhibition of PDE type IV can lead to inhibition of inflammatory mediator release, e.g., in M. W. Verghese et al., *J. Mol. Cell Cardiol.*, 12 (Suppl. II), S 61, (1989) and airway smooth muscle relaxation, e.g., in T. J. Torphy, "Directions for New Anti-Asthma Drugs," eds S. R. O'Donnell and C. G. A. Persson, 1988, 37 Birkhauser-VeHag.

Thus, compounds such as the above-mentioned 8-cyclopentyl-6-ethyl-3-[substituted]-5,8-dihydro-4H-1,2,3a,7,8-pentaaza-as-indacenes which inhibit PDE type IV but have poor activity against other PDE types, are able to inhibit the release of inflammatory mediators and relax airway smooth muscle without causing undesired cardiovascular or antiplatelet effects. The 8-cyclopentyl-6-ethyl-3-[substituted]-5,8-dihydro-4H-1,2,3a,7,8-pentaaza-as-indacenes are also useful as inhibitors of TNF production, which is recognized to be involved in many infectious and auto-immune diseases. See, e.g., W. Friers, *FEBS Letters*, 285, 199, (1991). Furthermore, it has been shown that TNF is the prime mediator of the inflammatory response seen in sepsis and septic shock. See, e.g., C. E. Spooner et al., *Clinical Immunology and Immunopathology*, 62, S11, (1992).

SUMMARY OF THE INVENTION

The present invention is concerned with an improved method of preparing an 8-cyclopentyl-6-ethyl-3-[substituted]-5,8-dihydro-4H-1,2,3a,7,8-pentaaza-as-indacene compound of Formula (1.0.0):

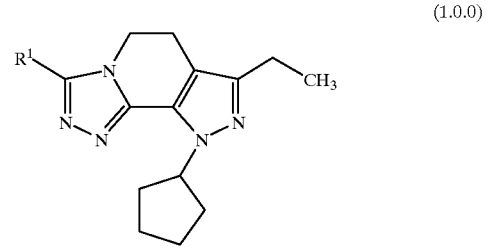

(1.0.0)

and pharmaceutically acceptable salt forms thereof, wherein:

$R^1$ is a member independently selected from the group consisting of hydrogen; ($C_1$–$C_6$) alkyl; ($C_1$–$C_4$) alkoxy; ($C_1$–$C_4$) alkoxy($C_1$–$C_4$) alkyl; ($C_2$–$C_8$) alkenyl; ($C_3$–$C_7$) cycloalkyl and 1'-methyl thereof; ($C_3$–$C_7$) cycloalkyl($C_1$–$C_2$) alkyl; a saturated or unsaturated ($C_4$–$C_7$) heterocyclic-($CH_2$)$_n$—group where n is an integer selected from 0, 1, and 2, comprising one or two heteroatoms independently selected from O, S, S(=O)$_2$, N, NR$^3$, O together with N or NR$^3$, S or S(=O)$_2$ together with N or NR$^3$, and N or NR$^3$ together with N or NR$^3$; where:

$R^3$ is hydrogen or ($C_1$–$C_4$) alkyl; or $R^1$ is a group of Formula (1.1.0):

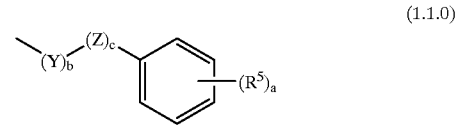

(1.1.0)

wherein:

a is an integer selected from 1 through 5, inclusive;

b and c are each independently an integer selected from 0 and 1;

$R^5$ is a member independently selected from the group consisting of hydrogen; hydroxy; ($C_1$$C_4$) alkyl; ($C_2$–$C_4$) alkenyl; ($C_1$–$C_4$) alkoxy; ($C_3$–$C_6$) cycloalkoxy; halogen; trifluoromethyl; $CO_2R^{3a}$; $CONR^{3a}R^{3b}$; $NR^{3a}R^{3b}$; $NO_2$; and $SO_2NR^{3a}R^{3b}$; where $R^{3a}$ and $R^{3b}$ are each independently selected from the group consisting of hydrogen and ($C_1$–$C_4$) alkyl;

Z is O, S, S(=O)2, C(=O), or NR$^3$; and

Y is —($C_1$–$C_4$) alkylene- or —($C_2$–$C_4$) alkenylene-, either of which is optionally mono-substituted by hydroxy; wherein:

each above-recited alkyl, alkenyl, cycloalkyl, alkoxyalkyl and heterocyclic group is substituted by 0 to 3 substituents comprising a member independently selected from group consisting of ($C_1$–$C_2$) alkyl, trifluoromethyl, and halogen;

comprising:

(a) subjecting a solventless reaction mixture of γ-caprolactone and p-methoxybenzylamine to heating whereby there is produced an amide compound N-protected by p-methoxybenzyl, of Formula (2.0.0):

(2.0.0)
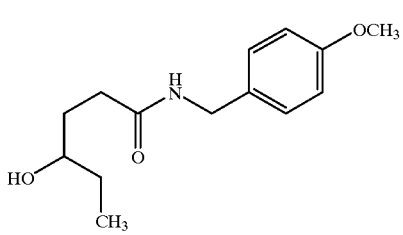

(b) reducing said amide compound of Formula (2.0.0) whereby there is produced an amino alcohol compound N-protected by p-methoxybenzyl, of Formula (3.0.0):

(3.0.0)
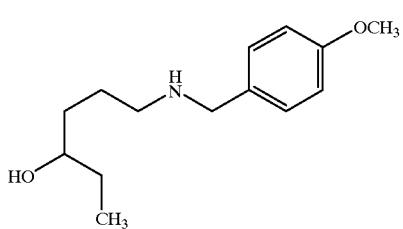

(c) acylating said aminoalcohol compound of Formula (3.0.0) with ethyl oxalyl chloride whereby there is produced an oxalamic acid ethyl ester compound N-protected by p-methoxybenzyl, of Formula (4.0.0):

(4.0.0)
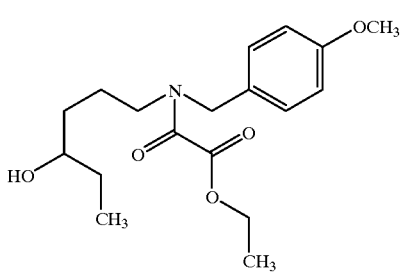

(d) oxidizing said oxalamic acid ethyl ester compound of Formula (4.0.0) whereby there is produced an oxalamide ketone compound N-protected by p-methoxybenzyl, of Formula (5.0.0)
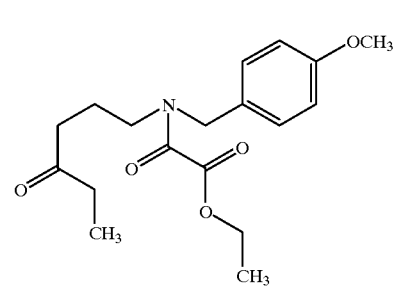

(e) ring closing said oxalamide ketone compound of Formula (5.0.0) whereby there is produced a pyridinone compound N-protected by p-methoxybenzyl, of Formula (6.0.0):

(6.0.0)
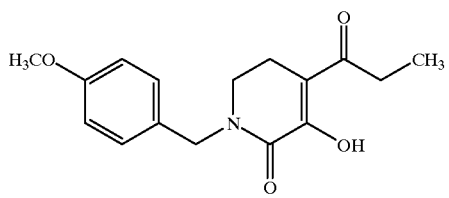

(f) O-methylating said pyridinone compound of Formula (6.0.0) whereby there is produced a 3-methoxy-pyridinone compound N-protected by p-methoxybenzyl, of Formula (7.0.0):

(7.0.0)
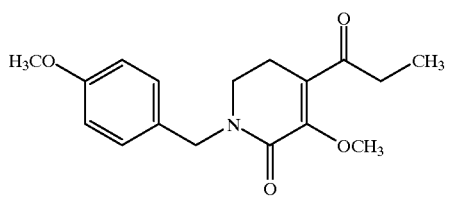

(g) treating said 3-methoxy-pyridinone compound of Formula (7.0.0) with cyclopentylhydrazine, whereby there is produced a pyrazolopyridinone compound N-protected by p-methoxybenzyl, of Formula (8.0.0):

(8.0.0)
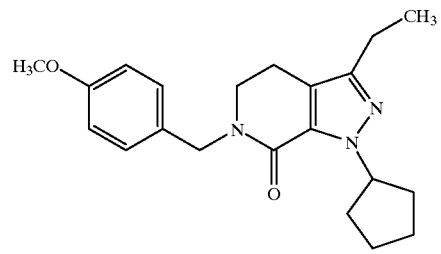

(h) deprotecting said pyrazolopyridinone compound of Formula (8.0.0) by removing said p-methoxybenzyl group therefrom, whereby there is produced a lactam compound of Formula (9.0.0):

(9.0.0)
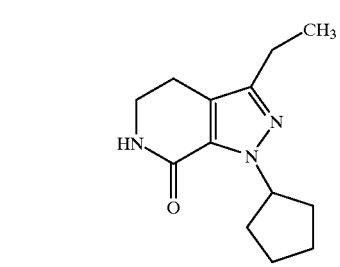

(i) esterifying said lactam compound of Formula (9.0.0) whereby there is produced a corresponding imino ester (imidate) compound of Formula (10.0.0):

(10.0.0)

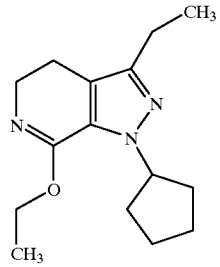

(j) treating said imino ester (imidate) compound of Formula (10.0.0) with a carboxylic hydrazide compound of Formula (11.0.0):

(11.0.0)

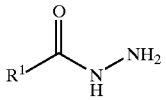

where $R^1$ has the same meaning as set out further above; whereby there is produced said 8-cyclopentyl-6-ethyl-3-[substituted]-5,8-dihydro-4H-1,2,3a,7,8-pentaaza-as-indacene compound of Formula (1.0.0).

The present invention is also concerned with several different groups of novel intermediates which are useful in the above-described process of preparing an 8-cyclopentyl-6-ethyl-3-[substituted]-5,8-dihydro-4H-1,2,3a,7,8-pentaaza-as-indacene compound of Formula (1.0.0). One group of such novel intermediates comprises tosylate and besylate salts of a pyrazolopyridinone compound N-protected by p-methoxybenzyl, of Formulas (8.1.0) and (8.1.1), respectively:

(8.1.0)

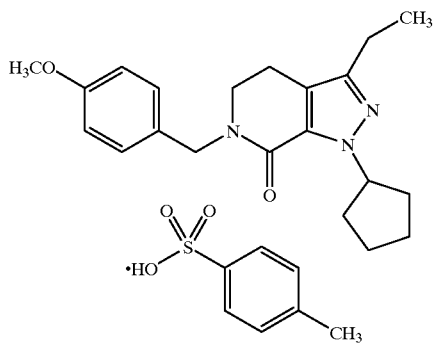

(8.1.1)

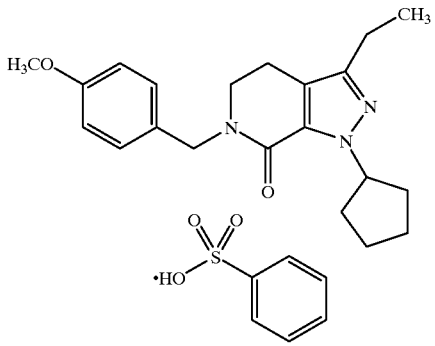

Another group of novel intermediates of the present invention comprises an imino ester (imidate) compound of Formula (10.1.0):

(10.0.0)

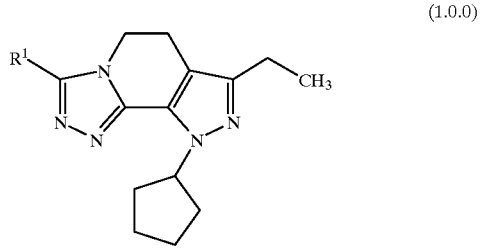

and pharmaceutically acceptable salt forms thereof, including especially the tosylate and besylate salts thereof.

DETAILED DESCRIPTION OF THE INVENTION

The improved process of preparation of the present invention is concerned with making therapeutically useful compounds of Formula (1.0.0):

(1.0.0)

and pharmaceutically acceptable salt forms thereof, wherein $R^1$ is, inter alia, a member independently selected from the group consisting of hydrogen; $(C_1-C_6)$ alkyl; $(C_1-C_4)$ alkoxy; $(C_1-C_4)$ alkoxy$(C_1-C_4)$ alkyl; $(C_2-C_8)$ alkenyl; $(C_3-C_7)$ cycloalkyl and 1'-methyl thereof; $(C_3-C_7)$ cycloalkyl$(C_1-C_2)$ alkyl; a saturated or unsaturated $(C_4-C_7)$ heterocyclic-$(CH_2)_n$—group where n is an integer selected from 0, 1, and 2, comprising one or two heteroatoms independently selected from O, S, S$(=O)_2$, N, $NR^3$, O together with N or $NR^3$, S or S$(=O)_2$ together with N or $NR^3$, and N or $NR^3$ together with N or $NR^3$; where $R^3$ is hydrogen or $(C_1-C_4)$ alkyl.

The above-recited compounds of Formula (1.0.0) are referred to collectively herein as 8-cyclopentyl-6-ethyl-3-[substituted]-5,8-dihydro-4H-1,2,3a,7,8-pentaaza-as-indacenes, and as already discussed, possess biological activity as inhibitors of PDE4 and TNF production. The improved method of preparation of the present invention is suitable for preparing said compounds where the $R^1$ moiety has the meaning of $(C_1-C_6)$ alkyl; $(C_1-C_4)$ alkoxy$(C_1-C_4)$ alkyl; $(C_2-C_8)$ alkenyl; $(C_3-C_7)$ cycloalkyl and 1' methyl thereof; or $(C_3-C_7)$ cycloalkyl$(C_1-C_2)$ alkyl. The expression "and 1'-methyl thereof" used in association with the $(C_3-C_7)$ cycloalkyl definition of $R^1$ means that optionally a methyl group is attached to the same carbon by which said $(C_3-C_7)$ cycloalkyl group is attached to the tricyclic nucleus of the compounds of Formula (1.0.0). As will be appreciated, such a definition of $R^1$ is readily distinguishable from the meaning "$(C_3-C_7)$ cycloalkyl$(C_1-C_2)$ alkyl", in which case an alkylene bridge, e.g., methylene, is interposed between said $(C_3-C_7)$ cycloalkyl group and said tricyclic nucleus. Accordingly, where $(C_3-C_7)$ cycloalkyl has the meaning of cyclohexyl, and a 1'-methyl group is present, $R^1$ will be defined as a moiety of Formula (1.2.0):

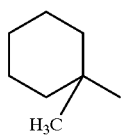

(1.2.0)

and will be named as 3-methyl-3-cyclohexyl.

In preferred embodiments, the method of the present invention is especially suitable for preparing compounds of Formula (1.0.0) where $R^1$ has the meaning of methyl, ethyl, n-propyl, iso-propyl, tert-butyl, cyclopentyl, cyclohexyl, and 3-methyl-3-cyclohexyl.

The improved method of preparation of the present invention is further suitable for preparing compounds of Formula (1.0.0) where the $R^1$ moiety has the meaning of a saturated or unsaturated $(C_4-C_7)$ heterocyclic-$(CH_2)_n$— group where n is an integer selected from 0, 1, and 2, comprising one or two heteroatoms independently selected from O, S, S(=O)$_2$, N, NR$^3$, O together with N or NR$^3$, S or S(=O)$_2$ together with N or NR$^3$, and N or NR$^3$ together with N or NR$^3$; where $R^3$ is hydrogen or $(C_1-C_4)$ alkyl.

In preferred embodiments, the method of the present invention is especially suitable for preparing compounds of Formula (1.0.0) where $R^1$ has the meaning of one of the following unsaturated $(C_5-C_6)$ heterocyclic-$(CH_2)_n$-groups:

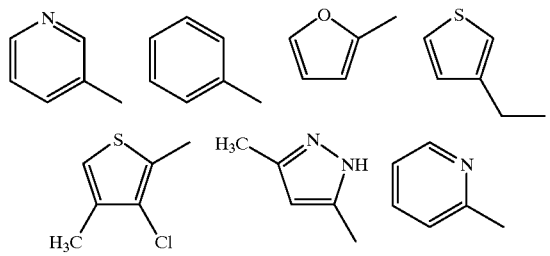

-continued

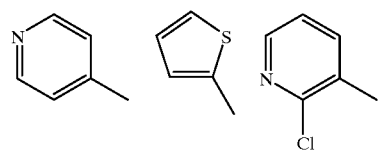

The improved method of preparation of the present invention is still further suitable for preparing compounds of Formula (1.0.0) where the $R^1$ moiety has the meaning of a group of Formula (1.1.0):

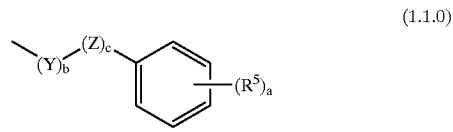

(1.1.0)

wherein: a is an integer selected from 1 through 5, inclusive; b and c are each independently an integer selected from 0 and 1; $R^5$ is a member independently selected from the group consisting of hydrogen; hydroxy; $(C_1-C_4)$ alkyl; $(C_2-C_4)$ alkenyl; $(C_1-C_4)$ alkoxy; $(C_3-C_6)$ cycloalkoxy; halogen; trifluoromethyl; $CO_2R^{3a}$; $CONR^{3a}R^{3b}$; $NR^{3a}R^{3b}$; $NO_2$; and $SO_2NR^{3a}R^{3b}$; where $R^{3a}$ and $R^{3b}$ are each independently selected from the group consisting of hydrogen and $(C_1-C_4)$ alkyl; Z is O, S, S(=O)$_2$, C(=O), or NR$^3$; and Y is —$(C_1-C_4)$ alkylene- or —$(C_2-C_4)$ alkenylene-, either of which is optionally mono-substituted by hydroxy.

In preferred embodiments, the method of the present invention is especially suitable for preparing compounds of Formula (1.0.0) where a is 1 or 2; b is 1; c is 0; Y is —$(C_1-C_2)$ alkylene-; and $R^5$ is methyl, methoxy, hydroxy, chloro, iodo, or trifluoromethyl. Accordingly, in more preferred embodiments of compounds especially suitable for preparation by the process of the present invention, $R^1$ has the meaning of one of the following groups:

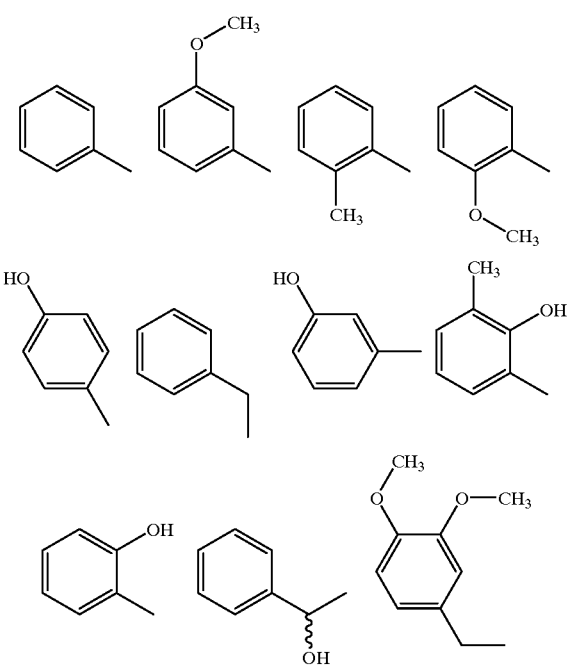

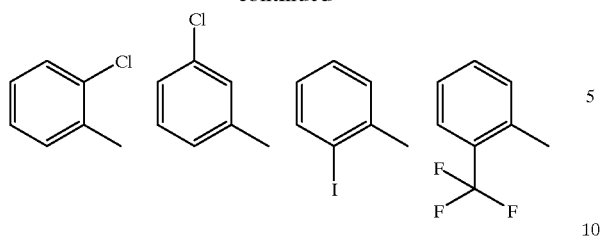
The improved process of the present invention for preparing a compound of Formula (1.0.0) may be illustrated by following reaction Scheme 2 which shows preparation of the species of Formula (1.0.0) where $R^1$ is 2-thienyl:
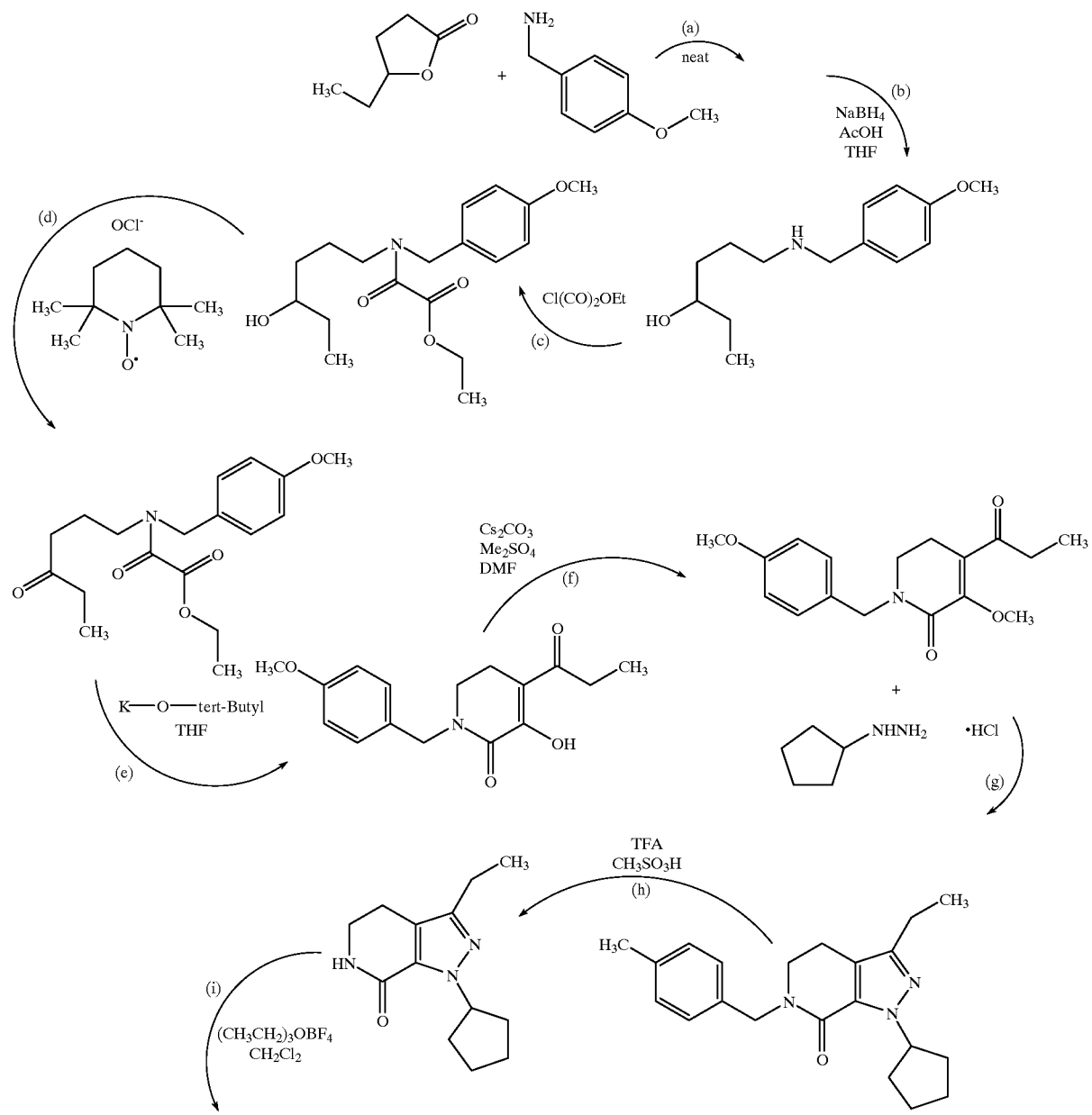
SCHEME 2

-continued

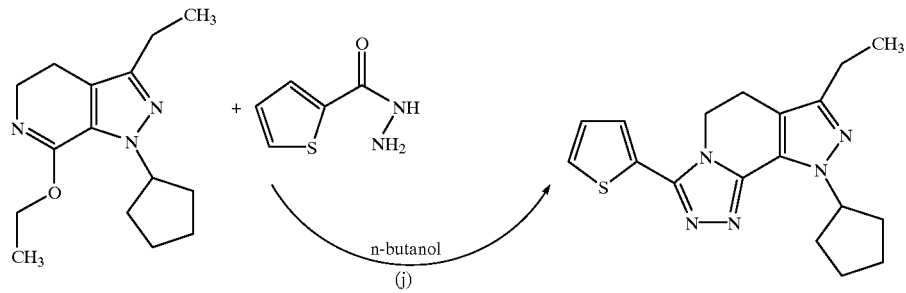

In the first step, Step (a) in Scheme 2 above-illustrated, there is formed a reaction mixture of γ-caprolactone and p-methoxybenzylamine which is subjected to heating in order to produce an amino alcohol compound N-protected by p-methoxybenzyl, of Formula (2.0.0) The reaction sequence of this Step (a) may be illustrated as follows:

The amide intermediate product of Formula (2.0.0) prepared in the above-described first step of the process of the present invention is next reduced to form the corresponding amino alcohol of Formula (3.0.0) which is N-protected by p-methoxybenzyl as already described. The reaction of Step (b) may be illustrated as follows:

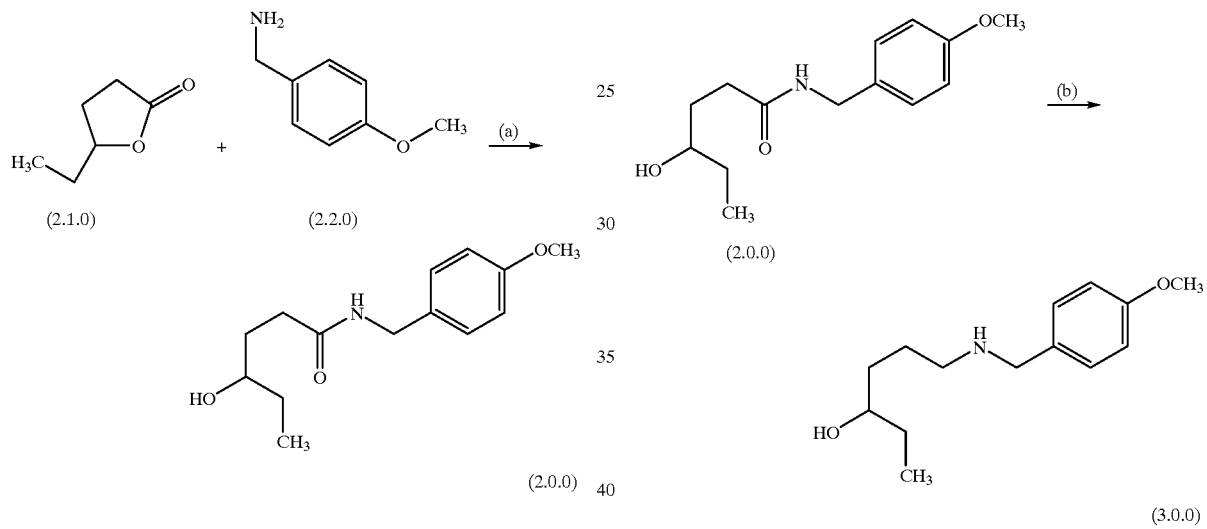

The γ-caprolactone of Formula (2.1.0) is reacted with the 4-methoxybenzylamine of Formula (2.2.0) neat, i.e., without a solvent, and heated to a temperature in the range of 70° to 950° C., preferably from 80° to 850° C. and held at that temperature for from 12 to 24 hours, preferably 16 hours. The amide product of Formula (2.0.0) is obtained using conventional separation procedures as a crystalline solid. This step improves upon such procedures as, e.g., reduction of the γ-caprolactone of Formula (2.1.0) using di-iso-butylaluminum hydride (DiBAl-H) in methylene chloride followed by reductive amination of the resulting lactol with p-methoxybenzylamine and sodium triactoxyborohydride [NaHB(OAc)$_3$], in terms of the elimination of the reducing agent and solvent which would otherwise have been required in the first step.

The second step also results in the production of a more stable amino alcohol intermediate product of Formula (3.0.0). It is to be noted that the p-methoxybenzylamine reactant of Formula (2.2.0) has been employed, rather than the corresponding p-methoxyphenylamine. It has been found that where such a p-methoxyphenyl group replaces the p-methoxybenzyl group attached to the nitrogen atom of the amino alcohol intermediate of Formula (3.0.0), that the resulting compound is unstable when exposed to ultraviolet (UV) radiation. The step involved in this reaction, Step (b) in Scheme 2 above, is described in the paragraph immediately below.

The above-illustrated reduction carried out in Step (b) is that of an N-substituted amide to the corresponding amine and is accomplished using a reducing agent for amides. Such reducing agents are known to the artisan and usually consist of the hydride type, e.g., borane-ammonia complex, $BH_3 \cdot NH_3$; borane-tert-butylamine complex, $(CH_3)_3CNH_2 \cdot BH_3$; borane-trimethylamine complex, $(CH_3)_3N \cdot BH_3$; aluminum hydride, $AlH_3$; sodium bis(2-methoxyethoxy)aluminum hydride, $[(CH_3OCH_2CH_2O)_2AlH_2]Na$; or sodium borohydride, $NaBH_4$.

The preferred reducing agent is sodium borohydride, $NaBH_4$, while other reducing agents are less preferred, e.g., lithium aluminum hydride, $LiAlH_4$, because it would produce too vigorous a reaction. The reducing agent is used in conjunction with a proton source which is added subsequently, and which is preferably a weak acid or THF solution of such an acid, e.g., acetic acid. The reducing agent and proton source are added to a suitable solvent such as methanol, ethanol, diethylether, formic acid, acetic acid, formamide, and tetrahydrofuran, THF. The preferred solvent is THF.

In the preferred manner of carrying out Step (b) the sodium borohydride reducing .agent is added to the THF solvent, after which the 4-hydroxyhexanoic acid 4-benzylamide of Formula (2.0.0) prepared in Step (a) is added as a solid. The reaction mixture is thereafter cooled, acetic acid in THF is added, and the reaction mixture is heated to a gentle reflux temperature in the range of 60° to 70° C. for a period of time from 14 to 18 hours, preferably 16 hours. Hydrogen gas is removed during the reaction and unreacted amide is removed by extraction with ethyl acetate after addition of 1N HCl to decompose excess reagent. Thereafter, the pH of the reaction mixture is raised to 11 in order to permit the amino alcohol intermediate product of Formula (3.0.0) to be extracted into ethyl acetate and held for use in the succeeding Step (c).

Step (c) of the process of the present invention may be illustrated by the following reaction scheme:

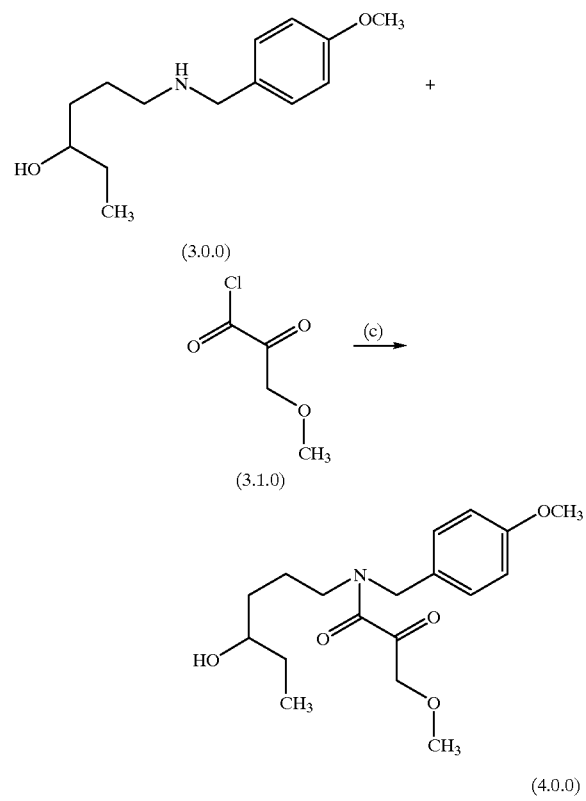

The above-illustrated acylation carried out in Step (c) is that of an amine with an acid chloride in an aqueous alkaline solution in accordance with the well-known conditions of the "Schotten-Baumann reaction". See Schotten, Ber. 17, 2544 (1884); and Georg, Bioorg. Med. Chem. Letters,.4, 335 (1994). The aqueous alkali is added in order to combine with the HCl which is liberated during the reaction. In a preferred manner of carrying out the acylation reaction of Step (c) an aqueous solution of sodium bicarbonate is utilized for this purpose. An additional solvent, preferably ethyl acetate, is employed to prepare a solution of the ethyl oxalyl chloride reactant of Formula (3.1.0), since the reaction mixture began as an ethyl acetate solution of the amino alcohol intermediate product of Formula (3.0.0), prepared in Step (b).

The acid chloride reactant used in Step (c) is ethyl oxalyl chloride of Formula (3.1.0). The reaction is exothermic; accordingly, the ethyl oxalyl chloride is added over time, preferably from 20 to 30 minutes, while at the same time the reaction temperature is preferably maintained at 0° to 5° C. The reaction is complete within a short period of time of from 1 to 2 hours, but the reaction mixture is optionally stirred at room temperature of from 20° to 25° C. for an additional period of time of from 14 to 18 hours, preferably 16 hours, in order to permit any residual ethyl oxalyl chloride which is unreacted to be removed by decomposition. The product of Formula (4.0.0), an oil, is obtained using conventional separation procedures, and is structurally an oxalamic acid ethyl ester which is N-protected by the p-methoxy benzyl group. This intermediate product is used as the starting material in the next step essentially without additional purification.

Step (d) of the process of the present invention may be illustrated by the following reaction scheme:

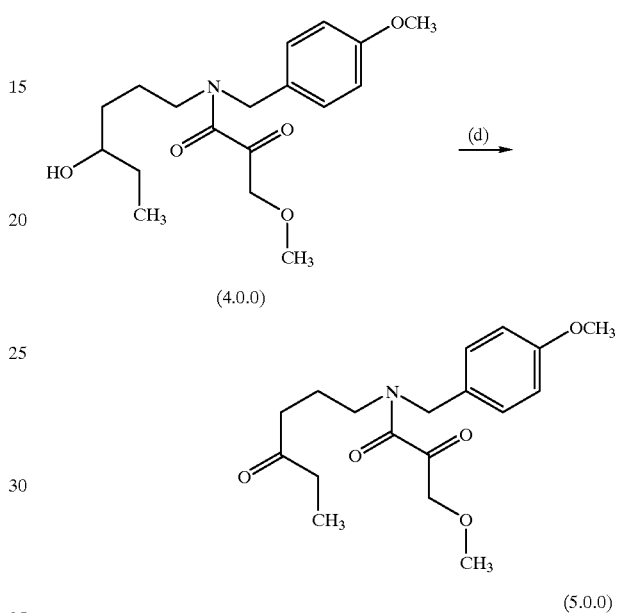

The above-illustrated oxidation carried out in Step (d) is that of a secondary alcohol moiety to a keto moiety, which may be carried out using strong oxidizing agents under suitable oxidation conditions in accordance with methods of which the artisan is well aware. For example, the "Jones oxidation reaction", which is carried out in the presence of chromic acid, aqueous sulfuric acid, and acetone, is suitable. See, e.g., Bowden et al., J. Chem. Soc., 39 (1946); or Ley and Madin, Comp. Org. Syn., 7, 253–256 (1991). The method is especially useful since it proceeds rapidly with high yields and does not disturb any of the other double bonds present. The method is also very straightforward since it only requires that the secondary alcohol of Formula (4.0.0) be dissolved in acetone and then titrated with the "Jones reagent" consisting of a solution of chromic acid and sulfuric acid in water.

Another type of oxidation process suitable for use in Step (d) of the present invention is that involving the use of acid dichromate, $H_2CrO_4$; and various other oxidation catalyst compositions involving chromium, e.g., chromic oxide, $Cr_2O_3$; chromic hydroxide, $Cr(OH)_3.nH_2O$; chromic acetate, $Cr(CH_3COO)_3$. See Cainelli; Cardillo Chromium Oxidations in Organic Chemistry; Springer: New York, 1984 for further details concerning chromium oxidation catalysts and procedures for using them. Another well-known process for oxidizing secondary alcohols to ketones which is suitable for carrying out Step (d) is the "Sarett oxidation reaction", which uses a $CrO_3$-pyridine complex as the oxidation catalyst. See, e.g., Poos et al, J. Am. Chem. Soc. 75, 422 (1953); or Hasan and Rocek, J. Am. Chem. Soc., 97, 1444, 3762 (1975).

Other types of strong oxidation catalysts and procedures for using them to convert a secondary alcohol such as that of Formula (4.0.0) to the corresponding ketone, such as that of Formula (5.0.0), include but are not limited to potassium permanganate, $KMnO_4$; bromine, $Br_2$; and ruthenium tetroxide, $RuO_4$.

A still further example of suitable oxidation catalysts and procedures for using them to convert a secondary alcohol of Formula (4.0.0) to the corresponding ketone of Formula (5.0.0), and one which is preferred for use in Step (d) of the process of the present invention include but are not limited to the use of sodium hypochlorite oxidizing agent in the presence of the catalyst 2,2,6,6-tetramethyl-1-piperidinyloxy, free radical (TEMPO). The structure of the TEMPO catalyst may be represented by the following Formula (4.1.0):

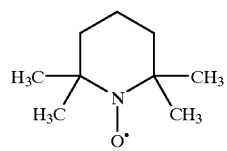

(4.1.0)

In this preferred manner of carrying out oxidation of the secondary alcohol of Formula (4.0.0) in order to convert it to the ketone of Formula (5.0.0), it is also preferred that the sodium hypochlorite solution be made fresh when carrying out Step (d) by dissolving calcium hypochlorite and sodium carbonate in water and adjusting the pH of the resulting solution to from 9.0 to 10.0, preferably 9.5 with sodium bicarbonate, followed by filtering of said solution to remove remaining calium carbonate side product in the solution.

Further in this preferred manner of carrying out Step (d), the reaction mixture comprises the secondary alcohol of Formula (4.0.0) dissolved in methylene chloride, $CH_2Cl_2$; and potassium bromide, KBr, dissolved in water. The TEMPO catalyst is added to the reaction mixture, which is then cooled to a temperature of 0° to 10° C., preferably 0° to 50° C., after which the sodium hypochlorite oxidizing agent is slowly added to the reaction mixture, which is maintained at a temperature of 10° to 20° C., preferably 100 to 15° C. The product is an oil, which is obtained using conventional separation procedures, and which is used in the next step of the process without additional purification.

A still more preferred manner of carrying out Step (d) as above-described, involves the use of a polymer to support the oxidizing agent, sodium hypochlorite as the active ion OCl⁻, and/or the TEMPO catalyst. See McKillop; Young, *Synthesis*, 401–422 (1979). Said still more preferred manner of carrying out Step (d) also involves the use of phase transfer catalysis, since the reaction taking place is a nucleophilic substitution in which the substrate is relatively insoluble in water and other polar solvents, while the nucleophile is an anion which is soluble in water but not in the substrate or other organic solvents. See Dehmlow; Dehmlow *Phase Transfer Catalysis*, 2$^{nd}$ ed.; Verlag Chemie: Deerfield Beach, Fla. (1983).

Step (e) of the process of the present invention may be illustrated by the following reaction scheme:

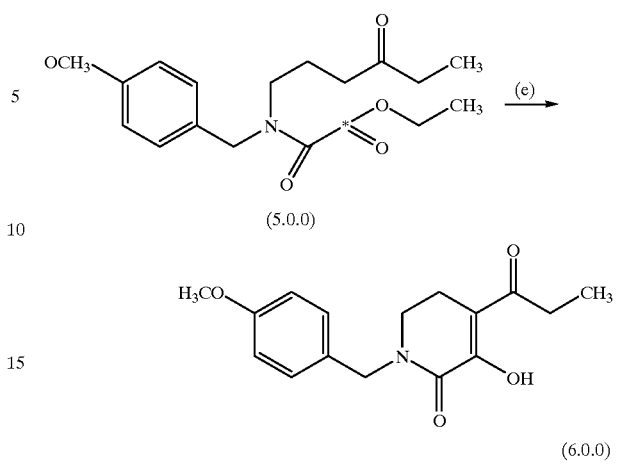

(5.0.0)

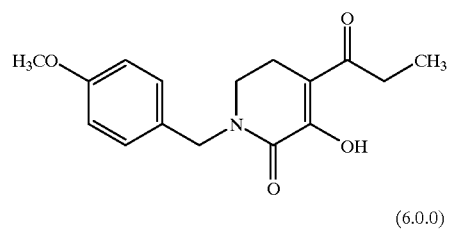

(6.0.0)

The above-illustrated ring closure carried out in Step (e) comprises a base-catalyzed cyclization of dicarboxylic acid esters to form a β-keto ester. The asterisk ("*") in the dicarboxylic acid of Formula (5.0.0) indicates the point of separation of one of the esters to form an ethanol side product not shown in the above-recited reaction scheme. The ring closure involved is an organic name reaction referred to as the "Dieckmann condensation reaction". See Dieckmann, Ber. 27, 102, 965 (1894); or Davis and Garrett, *Comp. Org. Syn.* 2, 806–829 (1991).

The reaction is carried out in the presence of a relatively strong base such as sodium ethoxide or potassium tert-butoxide, and in a suitable solvent, e.g., dry tetrahydrofuran, di-iso-propyl ether, methyl tert-butyl ether, and toluene. The base is added gradually over a period of 15 to 45 minutes, preferably 30 minutes, while the reaction mixture temperature is kept below from 30° to 40° C., preferably below 35° C. Thereafter, the reaction proceeds to completion in from 0.5 to 1.5 hours, usually 1.0 hour with the reaction mixture being at room temperature, ie., from 20° to 25° C. The product, a solid, is isolated by filtration.

Step (f) of the process of the present invention may be illustrated by the following reaction scheme:

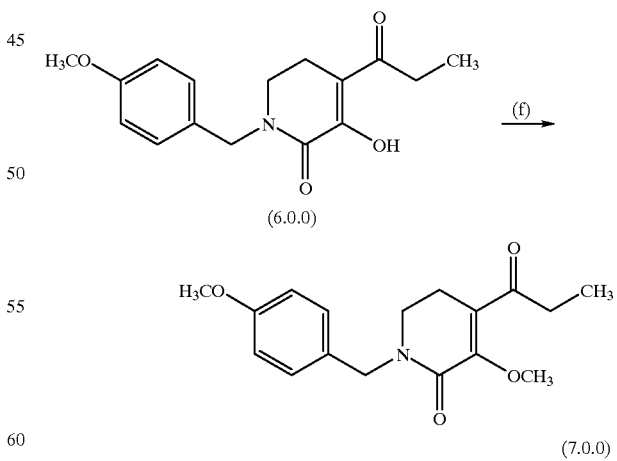

(6.0.0)

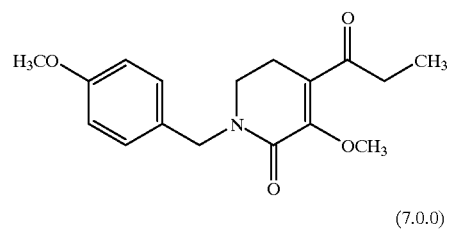

(7.0.0)

The above-illustrated reaction involves the O-methylation of a pyridinone compound of Formula (6.0.0) whereby there is produced a 3-methoxy-pyridinone compound N-protected by p-methoxybenzyl, of Formula (7.0.0). It is desirable to obtain selective O-methylation of the alcohol group without corresponding C-methylation; consequently, some reactions have proved unsuitable, e.g., treatment with methyl iodide in acetone with potassium carbonate.

One successful approach, which represents a preferred embodiment of the process of the present invention, is alkylation of the alcohol group with an inorganic ester, specifically, methylation with dimethylsulfate. In a preferred embodiment, this reaction is carried out in dimethylformamide (DMF) as a solvent in the presence of cesium carbonate, $Cs_2CO_3$, with gradual addition of the dimethylsufate over a period of 15 to 45 minutes, preferably 30 minutes, while the reaction mixture temperature is kept at from 15° to 30° C., preferably from 20° to 25° C. Thereafter, the reaction mixture is maintained at this temperature and stirred for from 12 to 20 hours, usually 16 hours. The product, an oil, is obtained using conventional separation procedures.

Step (g) of the process of the present invention may be illustrated by the following reaction scheme:

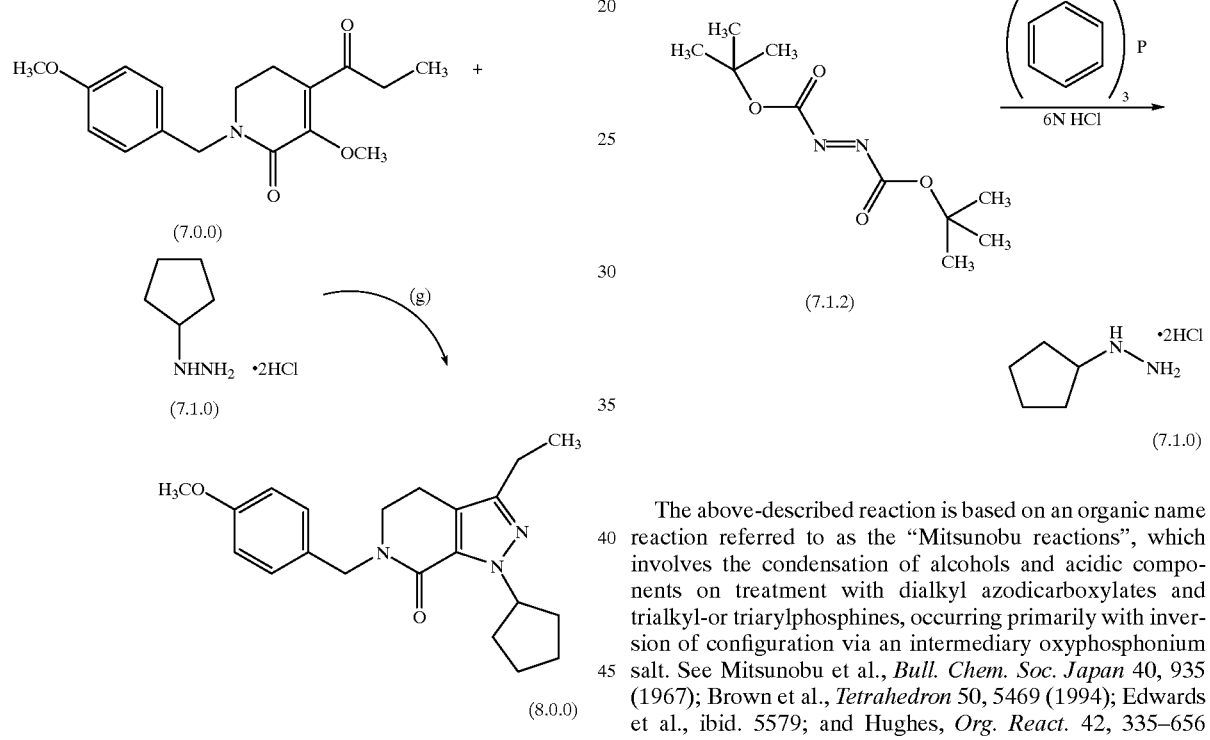

The above-illustrated reaction involves preparation of the pyrazole-containing compound of Formula (8.0.0) by treating the 3-methoxy-pyridinone compound of Formula (7.0.0) with the cyclopentylhydrazine dihydrochloride of Formula (7.1.0). In a preferred embodiment, this reaction is carried out in tetrahydrofuran (THF) solvent with heating of the reaction mixture to from 75° to 95° C., preferably 88° C., for from 8 to 16 hours, preferably 12 hours, while the reaction mixture is being swept by nitrogen in order to remove methanol, THF, and HCl. The product is a thick, dark oil which may be used in the next step of the process of the present invention without further treatment, or which alternatively, may be purified as a p-toluenesulfonic acid or benzenesulfonic acid salt, using conventional separation procedures.

Where the compound of Formula (8.0.0) is to be purified as the p-toluenesulfonic acid or benzenesulfonic acid salt, in a preferred embodiment it is dissolved in ethyl acetate and treated with anhydrous p-toluenesulfonic acid or anhydrous benzenesulfonic acid dissolved in ethyl acetate. The respective salt crystallizes from the reaction mixture, which is then cooled and filtered to provide the pure tosylate or benzenesulfonate salt.

A key reactant in Step (g) described above is the cyclopentylhydrazine dihydrochloride of Formula (7.1.0), which may be prepared in accordance with several methods known in the literature. In a preferred embodiment, the method described in *Syn. Comm.* 11, 43 (1981) is used in which cyclopentanol is treated with di-teit-butylazodicarboxylate and triphenylphosphine in accordance with the reaction scheme which may be illustrated as follows:

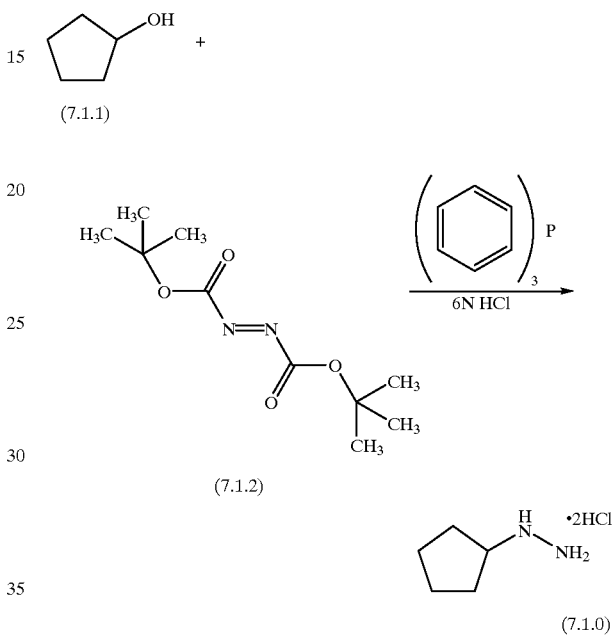

The above-described reaction is based on an organic name reaction referred to as the "Mitsunobu reactions", which involves the condensation of alcohols and acidic components on treatment with dialkyl azodicarboxylates and trialkyl-or triarylphosphines, occurring primarily with inversion of configuration via an intermediary oxyphosphonium salt. See Mitsunobu et al., *Bull. Chem. Soc. Japan* 40, 935 (1967); Brown et al., *Tetrahedron* 50, 5469 (1994); Edwards et al., ibid. 5579; and Hughes, *Org. React.* 42, 335–656 (1992).

In a preferred embodiment for the preparation of the cyclopentylhydrazine dihydrochloride of Formula (7.1.0), the cyclopentanol of Formula (7.1.1) and triphenylphosphine are dissolved together in a suitable solvent such as tetrahydrofuran (THF), and thereafter the reaction mixture is cooled to a temperature of from 2° to 8° C., preferably 5° C. Di-tert-butylazodicarboxylate dissolved in THF is then added to the reaction mixture over a period of from 1 hour to 3 hours, preferably 2 hours, while the temperature of the reaction mixture is kept below 6° C. The reaction mixture is permitted to rise to room temperature, i.e., 20° to 25° C. and is stirred for from 4 hours to 6 hours, preferably 5 hours, whereafter 6N HCl is added to the reaction mixture in order to remove the BOC groups from the product. The reaction mixture is then stirred for an additional period of from 18 to 30 hours, preferably 24 hours. A solid product is then isolated as the dihydrochloride salt using conventional separation procedures. It should be noted that the major product may be either the dihydrochloride salt or the monohydrochloride salt, depending upon the stoichiometry of the amount of 6N HCl which is added. Either salt performs well in the reaction of above-described Step (g).

Step (h) of the process of the present invention may be illustrated by the following reaction scheme:

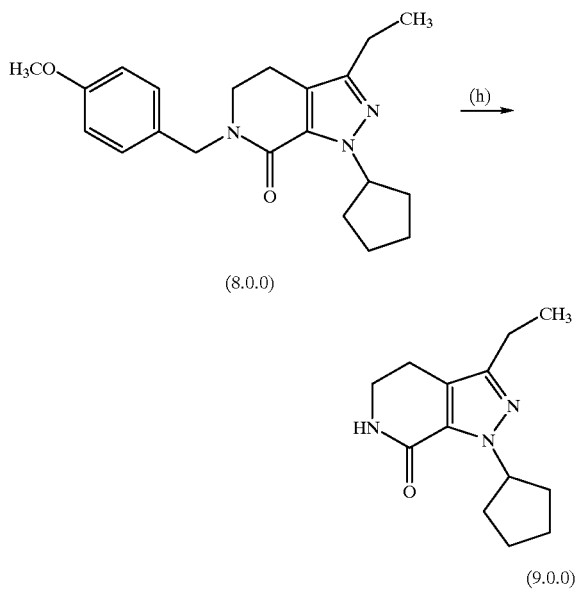

The above-illustrated reaction involves deprotection of the pyrazolopyridinone compound of Formula (8.0.0) by removal of the p-methoxybenzyl group therefrom, whereby there is formed the lactam compound of Formula (9.0.0). Removal of the p-methoxybenzyl group is accomplished in accordance with well known methods for the deprotection of amines where the protecting group is a p-methoxybenzyl group. It is further noted that the reaction of Step (g) described in detail further above, and the deprotection of Step (h) may be carried out without isolation of the product of Step (g), i.e., both reactions may be carried out in tandem in the same reaction vessel.

In accordance with a preferred embodiment of the process of the present invention, Step (h) is carried out at a temperature of from 50° to 60° C., preferably 55° C., which ordinarily requires cooling of the reaction mixture after the completion of Step (g). Thereafter, trifluoroacetic acid (TFA) is added slowly to the reaction mixture while its temperature is maintained at from 50° to 60° C., the initial charge of TFA causing exothermic reaction conditions which require external cooling. Methanesulfonic acid, $CH_3SO_3H$, is next added to the reaction mixture, the temperature of which is now raised to from 65° to 75° C., preferably 70° C., at which temperature the reaction mixture is maintained for from 1½ to 2½ hours, preferably 2 hours. Thereafter the reaction mixture is cooled to a temperature of from 15° to 30° C., preferably 20° to 25° C., after which a solid product lactam of Formula (9.0.0) is obtained by conventional separation procedures.

Step (i) of the process of the present invention may be illustrated by the following reaction scheme:

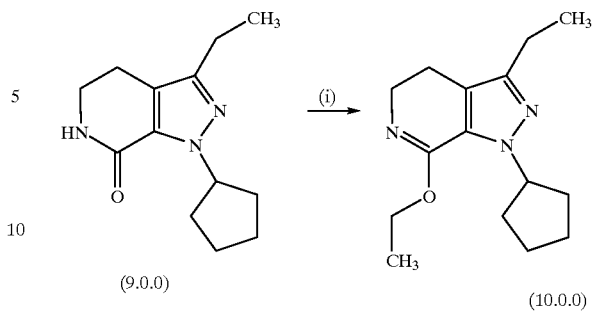

The above-illustrated reaction involves esterification of the lactam compound of Formula (9.0.0) to the corresponding imino ester, i.e., imidate compound of Formula (10.0.0). This esterification is accomplished by using triethyloxonium tetrafluoroborate, $(CH_3CH_2)_3OBF_4$, an agent used in the preparation of ω-aminoesters from lactams. See *Synth. Commun.* 18, 1625 (1988).

In a preferred embodiment of the process of the present invention for carrying out Step (i), a solution of triethyloxonium tetrafluoroborate, $(CH_3CH_2)_3OBF_4$ in methylene chloride is slowly added to a suspension of the lactam compound of Formula (9.0.0) in methylene chloride over a period of from 30 to 50 minutes, preferably 40 minutes. Thereafter, the reaction mixture is maintained at a temperature of from 15° to 25° C., preferably from 18° to 22° C., for a period of from 18 to 24 hours, preferably 21 hours. The product, an oil, is obtained using conventional separation procedures.

Step (j) of the process of the present invention may be illustrated by the following reaction scheme:

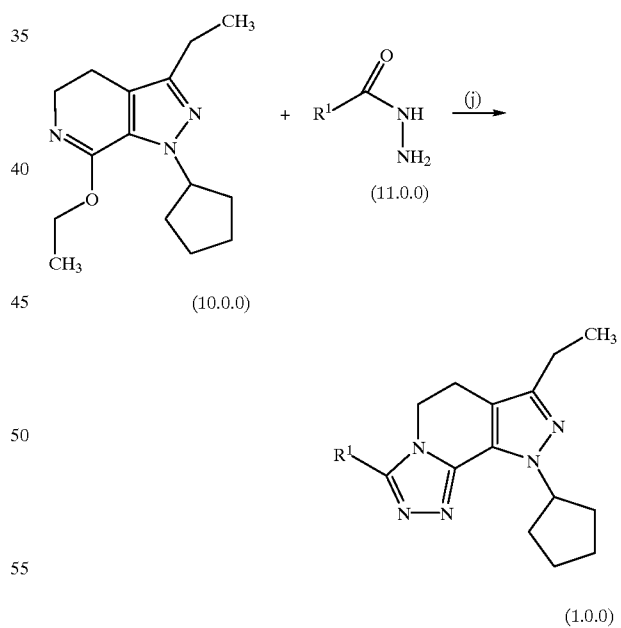

In a preferred embodiment of the process of the present invention for carrying out Step (j), a solution of the compound of Formula (10.0.0) in 1-butanol, and of 2-thiophenecarboxylic hydrazide, or alternatively, of 2,2-dimethylpropionic carboxylic hydrazide, is heated at a temperature from 85° to 95° C., preferably 90° C. over a period of from 36 to 60 hours, preferably 48 hours. The product, a white solid and an off-white solid, respectively, is obtained using conventional separation procedures.

The choice of solvent in which to dissolve the compound of Formula (10.0.0) and the particular carboxylic hydrazide which is to be used to prepare the desired compound of Formula (1.0.0), is dependent largely upon the ability of the candidate solvent to adequately dissolve the above-mentioned reactants, as well as to have a desirably low boiling point so that the reaction mixture can be refluxed for long periods of time without danger of degrading either the reactants or the final product. The solvent should be available in high purity and at a reasonable cost. 1-Butanol is especially suitable as a solution of 63% alcohol and 37% water, which forms a constant boiling mixture boiling at 92° C. Other suitable solvents include those selected from the group consisting of n-amyl ether, iso-amyl acetate, isopentyl alcohol, and iso-propyl alcohol.

It will be observed that Steps (a) through (i) of the process of the present invention, described in detail further above, all and each relate to specific compounds transformed through each of the reactions recited in the above-mentioned Steps. These Steps, accordingly, have no generic implications. The next and above-illustrated last step, Step (j), on the other hand, is the point in the process of the present invention where the different substituents which define the $R^1$ group are introduced into the structure of the final product defined by Formula (1.0.0). Thus, the last step intermediate, and consequently a key intermediate, in the process of the present invention comprises the imino ester (imidate) compound of Formula (10.0.0):

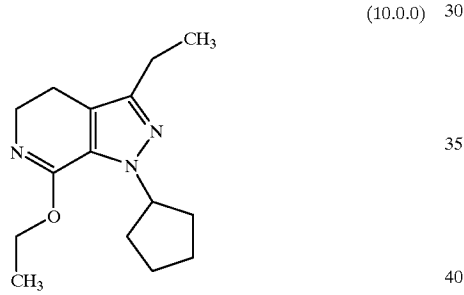

(10.0.0)

and pharmaceutically acceptable salt forms thereof, including especially the tosylate and besylate salts thereof.

The key, last step intermediate of Formula (10.0.0) is reacted with a hydrazine of appropriate structure to provide the desired meaning of $R^1$ in the final products of Formula (1.0.0). The reaction not only serves to insert the desired substituent $R^1$ into the compound of Formula (10.0.0), but it also serves to provide a further ring closure to form the "triazolyl" component of the tricyclic final product of Formula (1.0.0). As already indicated further above, the final products of Formula (1.0.0) have been referred to heretofore as being 5,6-dihydro-9H-pyrazolo[3,4-c]-1,2,4-triazolo[4,3-a]pyridines, although it is preferred herein to refer to said compounds of Formula (1.0.0) as being 8-cyclopentyl-6-ethyl-3-[substituted]-5,8-dihydro-4H -1,2,3a,7,8-pentaaza-as-indacenes.

The above-mentioned hydrazine of appropriate structure to provide the desired meaning of $R^1$ is a carboxylic hydrazide compound of Formula (11.0.0):

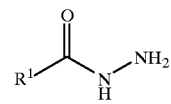

(11.0.0)

where $R^1$ has the same meaning as set out further above. In preferred embodiments of the present invention, the suitable carboxylic hydrazide compound of Formula (11.0.0) is a member selected from the group consisting of those recited as follows:

| $R^1$ | Hydrazide | Name | $R^1$ | Hydrazide | Name |
|---|---|---|---|---|---|
| 3-Methyl- | | Methyl-carboxylic hydrazide | 3-Pyridin-2-yl- | | 2-Pyridinyl-carboxylic hydrazide |
| 3-Ethyl- | | Ethyl-carboxylic hydrazide | 3-Pyridin-4-yl- | | 4-Pyridinyl-carboxylic hydrazide |
| 3-n-Propyl- | | n-Propyl-carboxylic hydrazide | 3-Thiophen-2-yl | | 2-Thiophene-carboxylic hydrazide |

-continued

| R¹ | Hydrazide | Name | R¹ | Hydrazide | Name |
|---|---|---|---|---|---|
| 3-iso-Propyl- | | iso-Propyl-carboxylic hydrazide | 3-(2-Chloro)-pyridin-3-yl- | | 3-(2-Chloro-pyridinyl)-carboxylic hydrazide |
| 3-tert-Butyl- | | Tert-butyl-carboxylic hydrazide | 3-(3-Methoxy)-phenyl- | | 3-Methoxy-phenyl-carboxylic hydrazide |
| 3-Cyclopentyl | | Cyclopentyl-carboxylic hydrazide | 3-(Tol-2-yl)- | | 2-Toluene-carboxylic hydrazide |
| 3-Cyclohexyl- | | Cyclo-hexyl-carboxylic hydrazide | 3-(2-Methoxy)-phenyl | | 2-Methoxy-phenyl-carboxylic hydrazide |
| 3-Methyl-3-cyclohexyl- | | Methyl-cyclohexyl-carboxylic hydrazide | 3-(4-Phenol)- | | 4-Phenol-carboxylic hydrazide |
| 3-Pyridin-3-yl- | | 3-Pyridinyl-carboxylic hydrazide | 3-Benzyl-ideneyl | | Benzyl-idene-carboxylic hydrazide |

-continued

| R¹ | Hydrazide | Name | R¹ | Hydrazide | Name |
|---|---|---|---|---|---|
| 3-Phenyl- | benzohydrazide structure | Phenyl-carboxylic hydrazide | 3-(3-Phenol)- | 3-hydroxybenzohydrazide structure | 3-Phenol-carboxylic hydrazide |
| 3-Furan-2-yl- | furan-2-carbohydrazide structure | 2-Furanyl-carboxylic hydrazide | 3-(2-Hydroxy-3-methyl)-phenyl- | 2-hydroxy-3-methylbenzohydrazide structure | (2-Hydroxy-3-methyl)-phenyl carboxylic hydrazide |
| 3-Thiophen-3-yl-methyl- | 2-(thiophen-3-yl)acetohydrazide structure | 3-Thiophene-methyl-carboxylic hydrazide | 3-(2-Phenol)- | 2-hydroxybenzohydrazide structure | 2-Phenol-carboxylic hydrazide |
| 3-(3-Chloro-4-methyl)-thiophen-2-yl- | 3-chloro-4-methylthiophene-2-carbohydrazide structure | 3-(3-Chloro-4-methyl-thiophene)-carboxylic hydrazide | 3-(1-Hydroxy-1-phenyl)-methyl- | 2-hydroxy-2-phenylacetohydrazide structure | (1-Hydroxy-1-phenyl)-methyl-carboxylic hydrazide |
| 3-(3-Methyl)-pyrazol-5-yl- | 3-methyl-1H-pyrazole-5-carbohydrazide structure | 5-(3-Methyl-pyrazole)-carboxylic hydrazide | 3-(3,4-Dimethoxy)-phenyl- | 3,4-dimethoxybenzohydrazide structure | 3,4-Dimethoxy-phenyl-carboxylic hydrazide |
| 3-(2-Chloro-phenyl)- | 2-chlorobenzohydrazide structure | 2-Chloro-phenyl-carboxylic hydrazide | 3-(2-Iodo-phenyl)- | 2-iodobenzohydrazide structure | 2-Iodo-phenyl-carboxylic hydrazide |
| 3-(3-Chloro-phenyl)- | 3-chlorobenzohydrazide structure | 3-Chloro-phenyl-carboxylic hydrazide | 3-(2-Trifluoro-methyl-phenyl)- | 2-(trifluoromethyl)benzohydrazide structure | 2-Trifluoro-methyl-phenyl-carboxylic hydrazide |

Many of the above-described carboxylic hydrazide reactants of Formula (11.0.0) are available commercially. For example, 2-thiophenecarboxylic hydrazide is available from Aldrich Chemical Company, St. Louis, Mo. 63178-9916, under catalog no. T3,261-1. Where a carboxylic hydrazide is not commercially available, e.g., the tert-butylcarboxylic hydrazide, it may be prepared using methods published in the technical literature and well known to the person of ordinary skill in the art of synthesizing such organic compounds. Such a method was developed for preparing the tert-butylcarboxylic hydrazide, which is more appropriately named 2,2-dimethylpropionic carboxylic hydrazide. That method is described below.

The method developed for preparing 2,2-dimethylpropionic carboxylic hydrazide is a modification of a method described in published European application EP 653 419 (1995) assigned to Shell Oil [*Chem. Abs.* 123: 32678b (1995)]. which utilizes pivalic acid, hydrazine hydrate, and catalytic $TiO_2$. The reaction was carried out using n-propanol as the solvent, along with 1 mol % of $Ti(i-PrO)_4$, which hydrolyzes immediately upon addition to the reaction mixture to give amorphous $TiO_2$ active catalyst. After the reaction mixture is refluxed for 24 hours, the n-propanol solvent is distilled from the reaction vessel, azeotropically removing water from the reaction mixture. After dilution of the reaction mixture with fresh n-propanol, the solid $TiO_2$ active catalyst can be filtered from the reaction mixture. The residue can be stripped and repulped in petroleum ether to give the desired 2,2-dimethylpropionic carboxylic hydrazide in high purity and in an 88% yield.

The present invention also relates to novel intermediate compounds utilized in the above-described process steps for preparing an 8-cyclopentyl-6-ethyl-3-[substituted]-5,8-dihydro-4H-1,2,3a,7,8-pentaaza-as-indacene compound of Formula (1.0.0). One group of such novel intermediates comprises a member selected from the group consisting of the tosylate and besylate salts of a pyrazolopyridinone compound N-protected by p-methoxybenzyl, of Formulas (8.1.0) and (8.1.1), respectively:

(8.1.0)

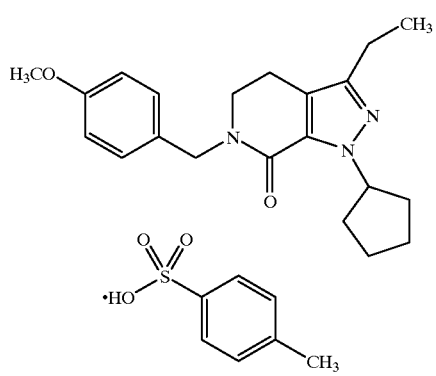

(8.1.1)

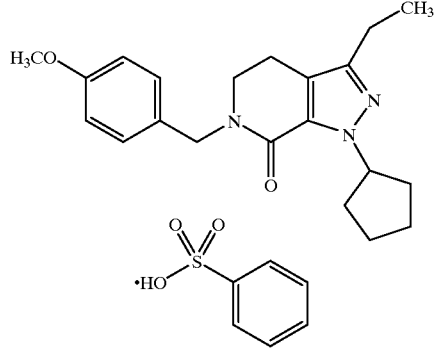

The above-described intermediate salts of Formula (8.1.0) and of Formula (8.1.1) are used in Step (h) as described in detail further above.

Another group of novel intermediates of the present invention comprises an imino ester (imidate) compound of Formula (10.0.0):

(10.0.0)

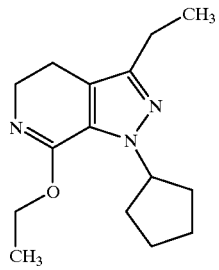

and pharmaceutically acceptable salt forms thereof, including especially the tosylate and besylate salts thereof. The tosylate and besylate salts may be represented by Formulas (10.1.0) and (10.2.0) as follows:

(10.1.0)

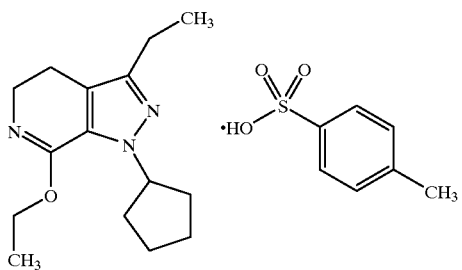

(10.2.0)

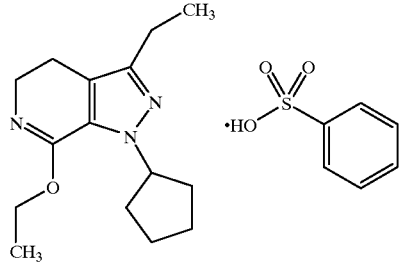

A further preferred embodiment of the present invention relates to a process for preparing compounds of Formula (1.0.0) consisting of only two steps, which commences with starting compounds of Formula (9.0.0), which are known as described in Scheme 1 detailed further above. This two step process may be represented by Scheme 3 as follows:

SCHEME 3

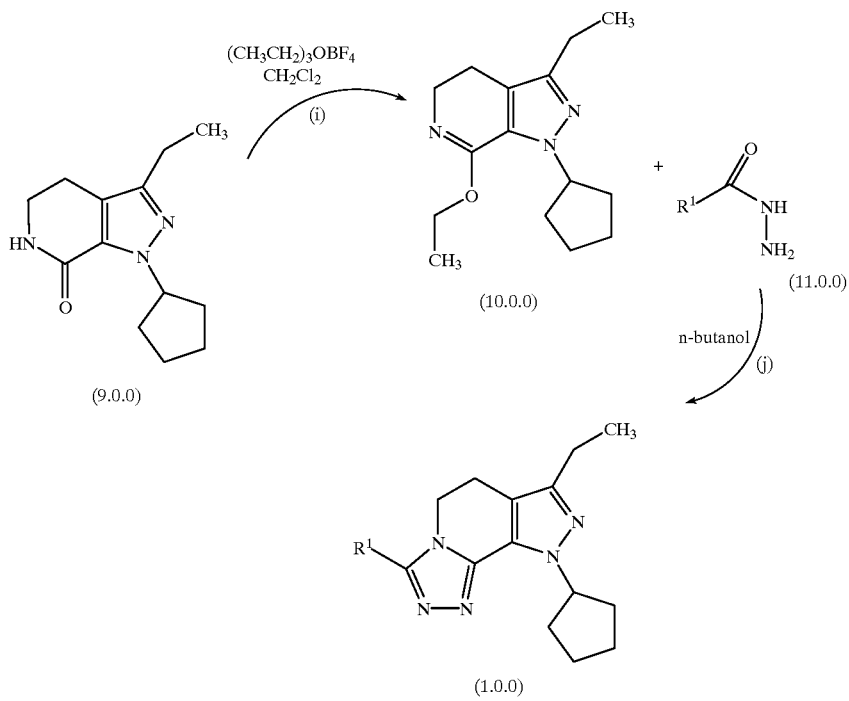

Accordingly, the present invention is further concerned with an improved method of preparing an 8-cyclopentyl-6-ethyl-3-[substituted]-5,8-dihydro-4H-1,2,3a,7,8-pentaaza-as-indacene compound of Formula (1.0.0):

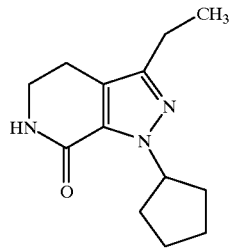

(1.0.0)

and pharmaceutically acceptable salt forms thereof, wherein $R^1$ is as defined further above; comprising:

(a) esterifying a lactam compound of Formula (9.0.0):

(9.0.0)

whereby there is produced a corresponding imino ester (imidate) compound of Formula (10.0.0):

(10.0.0)

(b) treating said imino ester (imidate) compound of Formula (10.0.0) with a carboxylic hydrazide compound of Formula (11.0.0):

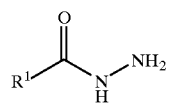

(11.0.0)

where $R^1$ has the same meaning as set out further above; whereby there is produced said 8-cyclopentyl-6-ethyl-3-[substituted]-5,8-dihydro-4H-1,2,3a,7,8-pentaaza-as-indacene compound of Formula (1.0.0).

A still further preferred embodiment of the present invention relates to a process for preparing compounds of Formula (1.0.0) consisting of a single step, which commences with the novel intermediate of Formula (10.0.0), which may be prepared in accordance with the process steps and procedures detailed further above. This single step process may be represented by Scheme 4 as follows:

SCHEME 4

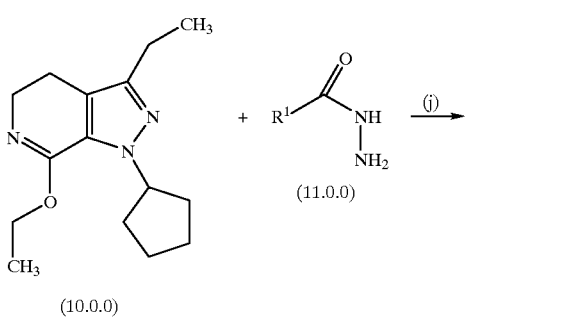

(10.0.0)

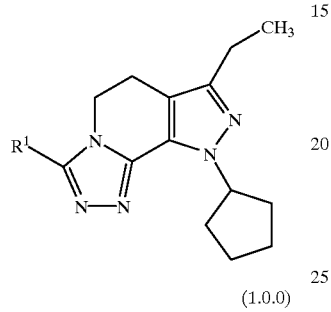

(1.0.0)

Accordingly, the present invention is yet further concerned with an improved method of preparing an 8-cyclopentyl-6-ethyl-3-[substituted]-5,8-dihydro-4H-1,2,3a,7,8-pentaaza-as-indacene compound of Formula (1.0.0):

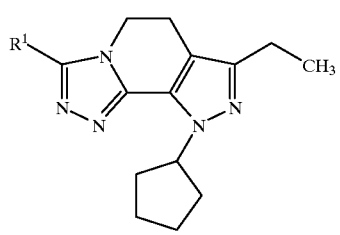

(1.0.0)

and pharmaceutically acceptable salt forms thereof, wherein $R^1$ is as defined further above; comprising:

treating an imino ester (imidate) compound of Formula (10.0.0):

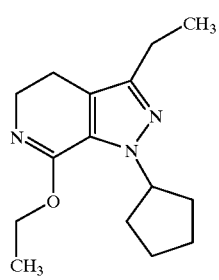

(10.0.0)

with a carboxylic hydrazide compound of Formula (11.0.0):

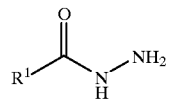

(11.0.0)

where $R^1$ has the same meaning as set out further above; whereby there is produced said 8-cyclopentyl-6-ethyl-3-[substituted]-5,8-dihydro-4H-1,2,3a,7,8-pentaaza-as-indacene compound of Formula (1.0.0).

Preferred embodiments for carrying out the various steps of the process of the present invention have been described herein. Accordingly, there are preferred embodiments for carrying out the overall process of the present invention. One of the more preferred of such preferred embodiments is described below.

An improved method of preparing an 8-cyclopentyl-6-ethyl-3-[substituted]-5,8-dihydro-4H-1,2,3a,7,8-pentaaza-as-indacene compound of Formula (1.0.0):

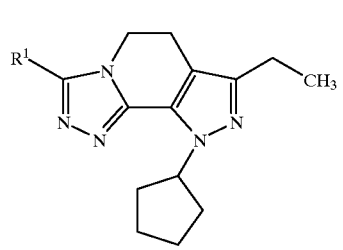

(1.0.0)

and pharmaceutically acceptable salt forms thereof, wherein $R^1$ is as defined further above; comprising:

(a) subjecting a solventless reaction mixture of γ-caprolactone and p-methoxybenzylamine to heating to a temperature in the range of 70° to 95° C., preferably from 80° to 85° C. and held at that temperature for from 12 to 24 hours, preferably 16 hours, whereby there is produced an amide compound N-protected by p-methoxybenzyl, of Formula (2.0.0):

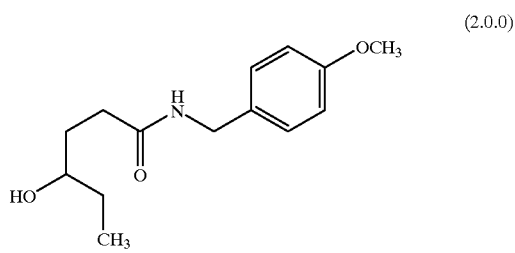

(2.0.0)

(b) reducing said amide compound of Formula (2.0.0) using a reducing agent selected from the group consisting of borane-ammonia complex, $BH_3 \cdot NH_3$; borane-tert-butylamine complex, $(CH_3)_3CNH_2 \cdot BH_3$; borane-trimethylamine complex, $(CH_3)_3N \cdot BH_3$; aluminum hydride, $AlH_3$; sodium bis(2-methoxyethoxy)aluminum hydride, $[(CH_3OCH_2CH_2O)_2AlH_2]Na$; and sodium borohydride, $NaBH_4$, preferably sodium borohydride;

said reducing agent being used in conjunction with a proton source comprising a weak acid or tetrahydrofuran (THF) solution of such an acid, preferably acetic acid; and said reducing agent and proton source being added to a solvent selected from the group consisting of methanol, ethanol, diethylether, formic acid, acetic acid, formamide, and tetrahydrofuran, THF, preferably THF;

wherein after said reducing agent is added to said solvent, said amide of Formula (2.0.0) is added as a solid to said reaction mixture which is thereafter cooled; said proton source in said solvent is added to said reaction mixture, which is then heated to a gentle reflux temperature in the range of 60° to 70° C. for a period of time from 14 to 18 hours, preferably 16 hours; hydrogen gas being removed as a byproduct and unreacted amide being removed by extraction with ethyl acetate after addition of 1N HCl in order to decompose excess reagent; and thereafter raising the pH of said reaction mixture to from 10 to 12, preferably 11 in order to permit the product of Formula (3.0.0) to be extracted into ethyl acetate and held for use in the next step;

whereby there is produced an amino alcohol compound N-protected by p-methoxybenzyl, of Formula (3.0.0):

(3.0.0)

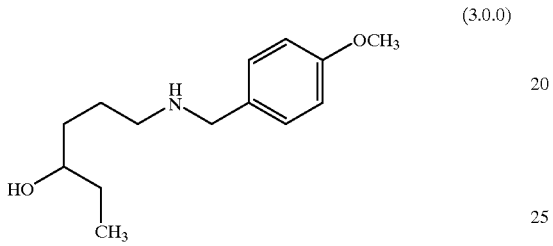

(c) acylating said amino alcohol compound of Formula (3.0.0) in accordance with Schotten-Baumann reaction conditions for treating an amine with an acid chloride in an aqueous alkaline solution, preferably an aqueous solution of sodium bicarbonate, wherein said acid chloride is preferably ethyl oxalyl chloride added as a solution in a solvent which is preferably ethyl acetate;

wherein the reaction which takes place is exothermic, whereupon said acid chloride, preferably ethyl oxalyl chloride, is added over time, preferably from 20 to 30 minutes, and said reaction temperature is maintained at 0° to 5° C. until said reaction is complete in from 1 to 2 hours; whereafter said reaction mixture is optionally stirred at from 20° to 25° C. for from 14 to 18 hours, preferably 16 hours, to permit unreacted acid chloride, preferably ethyl oxalyl chloride, to be removed by decomposition;

whereby there is produced an oxalamic acid ethyl ester compound N-protected by p-methoxybenzyl, of Formula (4.0.0):

(4.0.0)

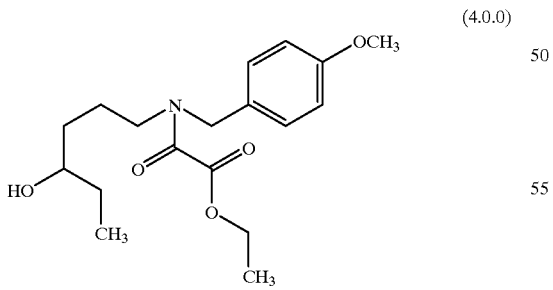

(d) oxidizing said oxalamic acid ethyl ester compound of Formula (4.0.0) using strong oxidizing agents under suitable oxidation conditions; wherein said oxidizing is accomplished:

(i) under Jones oxidation reaction conditions carried out in the presence of chromic acid, aqueous sulfuric acid, and acetone; or (ii) using sodium hypochlorite oxidizing agent in the presence of the catalyst 2,2,6,6-tetramethyl-1-piperidinyloxy, free radical (TEMPO), wherein said sodium hypochlorite solution be made fresh when carrying out said oxidizing, comprising: dissolving calcium hypochlorite and sodium carbonate in water and adjusting the pH of the resulting solution to from 9.0 to 10.0, preferably 9.5 with sodium bicarbonate, followed by filtering of said solution to remove remaining calcium carbonate side product in said solution; and further wherein a reaction mixture is established as a solution of said compound of Formula (4.0.0) in methylene chloride, $CH_2Cl_2$; in addition to potassium bromide, KBr, dissolved in water; to which said TEMPO catalyst is added and said reaction mixture is cooled to a temperature of from 0° to 10° C., preferably from 0° to 5° C.; after which said sodium hypochlorite oxidizing agent is slowly added while said reaction mixture is maintained at a temperature of from 10° to 20° C., preferably from 10° to 15° C.;

whereby there is produced an oxalamide ketone compound N-protected by p-methoxybenzyl, of Formula (5.0.0):

(5.0.0)

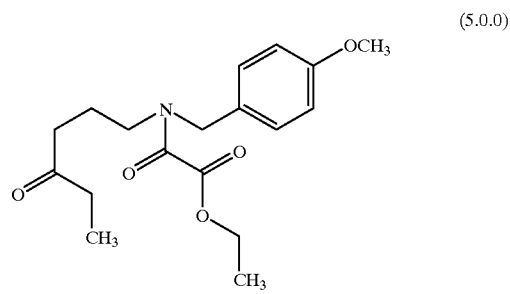

(e) ring closing said oxalamide ketone compound of Formula (5.0.0) under Dieckmann condensation reaction conditions, wherein a reaction is carried out in the presence of a relatively strong base selected from the group consisting of sodium ethoxide and potassium tert-butoxide, in a suitable solvent comprising dry tetrahydrofuran, di-iso-propyl ether, methyl tert-butyl ether, or toluene; wherein said base is added gradually over a period of 15 to 45 minutes, preferably 30 minutes, while said reaction mixture temperature is kept below from 30° to 40° C., preferably below 35° C., and said reaction proceeds to completion in from 0.5 to 1.5 hours, usually 1.0 hour with said reaction mixture being at from 20° to 25° C.;

whereby there is produced a pyridinone compound N-protected by p-methoxybenzyl, of Formula (6.0.0):

(6.0.0)

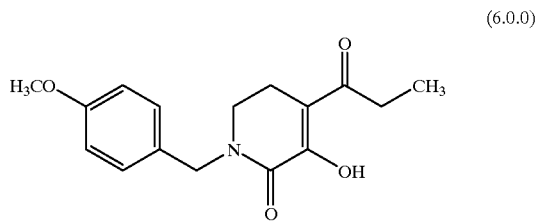

(f) O-methylating said pyridinone compound of Formula (6.0.0) by methylation with dimethylsulfate; wherein a reaction mixture is established with dimethylformamide (DMF)

solvent in the presence of cesium carbonate, $Cs_2CO_3$, with gradual addition of said dimethylsufate over a period of 15 to 45 minutes, preferably 30 minutes, while said reaction mixture temperature is kept at from 15° to 30° C., preferably from 20° to 25° C.; and thereafter, said reaction mixture is maintained at said temperature and stirred for from 12 to 20 hours, usually 16 hours;

whereby there is produced a 3-methoxy-pyridinone compound N-protected by p-methoxybenzyl, of Formula (7.0.0):

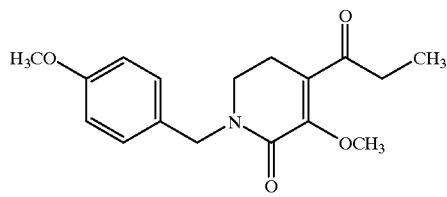

(7.0.0)

(g) treating said 3-methoxy-pyridinone compound of Formula (7.0.0) with cyclopentylhydrazine dihydrochloride; wherein a reaction mixture is established with tetrahydrofuran (THF) solvent and heating of said reaction mixture to 88° C., for 12 hours, while said reaction mixture is being swept by nitrogen in order to remove methanol, THF, and HCl; whereby there is produced a pyrazolopyridinone compound N-protected by p-methoxybenzyl, of Formula (8.0.0):

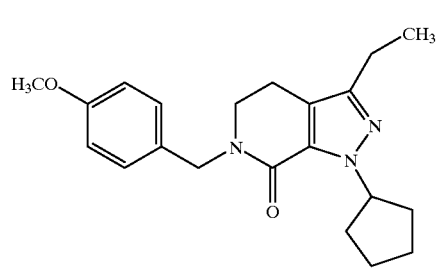

(8.0.0)

wherein said compound of Formula (8.0.0) may be used in the next step of the process without further treatment, or alternatively, may be purified as a p-toluenesulfonic acid or benzenesulfonic acid salt by dissolving said compound of Formula (8.0.0) in ethyl acetate and thereafter treating it with anhydrous p-toluenesulfonic acid dissolved in ethyl acetate or anhydrous benzenesulfonic acid dissolved in ethyl acetate; whereupon the respective salt crystallizes from the reaction mixture thus formed, which is then cooled and filtered to provide the pure tosylate or benzenesulfonate salt;

(h) deprotecting said pyrazolopyridinone compound of Formula (8.0.0) by removing said p-methoxybenzyl group therefrom; wherein a reaction mixture is established at a temperature of from 50° to 60° C., preferably 55° C.; after which trifluoroacetic acid (TFA) is added slowly, the initial addition of TFA causing exothermic reaction conditions which require external cooling; thereafter methanesulfonic acid, $CH_3SO_3H$, is added to said reaction mixture, the temperature of which is raised to from 65° to 75° C., preferably 70° C., at which temperature said reaction mixture is maintained for from 1½ to 2½ hours, preferably 2 hours; and thereafter said reaction mixture is cooled to a temperature of from 15° to 30° C., preferably 20° to 25° C.;

whereby there is produced a lactam compound of Formula (9.0.0):

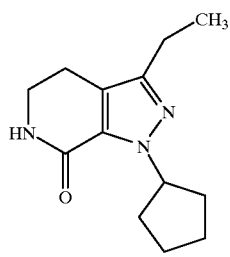

(9.0.0)

(i) esterifying said lactam compound of Formula (9.0.0) using triethyloxonium tetrafluoroborate, $(CH_3CH_2)_3OBF_4$; wherein a reaction mixture is established by slowly adding a solution of triethyloxonium tetrafluoroborate, $(CH_3CH_2)_3OBF_4$ in methylene chloride to a suspension of said lactam compound of Formula (9.0.0) in methylene chloride over a period of from 30 to 50 minutes, preferably 40 minutes; and thereafter, maintaining said reaction mixture at a temperature of from 15° to 25° C., preferably from 18° to 22° C., for a period of from 18 to 24 hours, preferably 21 hours;

whereby there is produced a corresponding imino ester (imidate) compound of Formula (10.0.0):

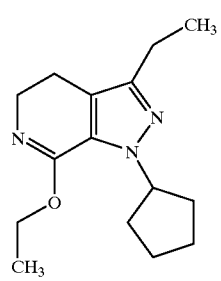

(10.0.0)

(j) treating said imino ester (imidate) compound of Formula (10.0.0) with a carboxylic hydrazide compound of Formula (11.0.0):

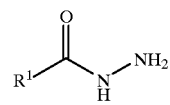

(11.0.0)

where $R^1$ is 2-thiophene or tert-butyl; wherein a reaction mixture is established with a solution of said compound of Formula (10.0.0) in 1-butanol, and of 2-thiophenecarboxylic hydrazide, or alternatively, of 2,2-dimethylpropionic carboxylic hydrazide; and said reaction mixture is heated at a temperature of from 85° to 95° C., preferably 90° C. over a period of from 36 to 60 hours, preferably 48 hours.

whereby there is produced 8-cyclopentyl-6-ethyl-3-thiophen-2-yl-5,8-dihydro-4H-1,2,3a,7,8-pentaaza-as-indacene of Formula (1.0.1), and 8-cyclopentyl-6-ethyl-3-t-butyl-5,8-dihydro-4H-1,2,3a,7,8-pentaaza-as-indacene of Formula (1.0.2):

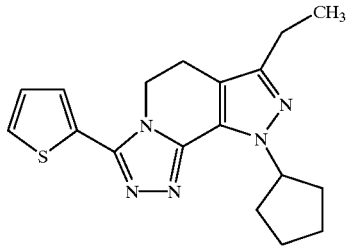

(1.0.1)

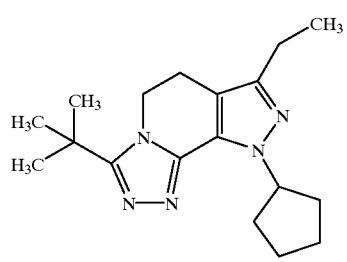

(1.0.2)

EXEMPLIFIED PREFERRED EMBODIMENTS OF THE INVENTION

There follows preparation and working examples of preferred embodiments of the present invention for the purpose of illustration and in order to make even more clear to the artisan the manner of carrying out the method of preparation of the present invention. However, the examples are intended only for the purpose of demonstrating the present invention to said artisan and should not be taken as in any way limiting the scope and contents of the present invention, to which end the appended claims are directed.

EXAMPLE 1
4-Hydroxyhexanoic acid 4-methoxybenzylamide (2.0.0)

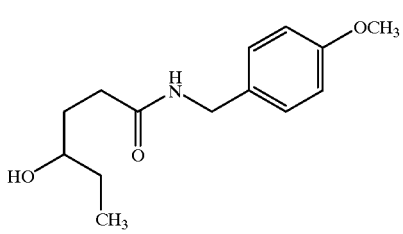

(2.0.0)

Gamma-caprolactone (28.745 Kg, 251.8 moles) and 4-methoxybenzylamine (38.0 Kg, 277 moles) were placed in a 100 gallon glass lined tank. The solution was heated to 80–85° C. and held at that temperature for 16 hours. TLC on silica gel plates showed the reaction was complete. The TLC system comprised: ethyl acetate with detection at 254 nm. Ethyl acetate (18 gal, 68 L) was slowly charged to the reaction pot after cooling to 60° C. Hexanes (a total of 18 gal, 68 L) were added until a haze was achieved. After ½ hour, to allow crystallization to start, the remainder of the hexanes was added. The slurry was cooled to 25° C. and granulated for 3 hours. The solid was collected by filtration and washed with a 1:1 mixture of ethyl acetate and hexanes. The wet cake was vacuum dried with no additional heat to produce 46.05 Kg (72.8%) of the desired amide; mp 81–82° C.

$^1$HMR (CDCl$_3$, 300 MHz) δ7.18 (d, 2), 6.84 (d, 2), 6.27 (bs, 1), 4.32 (d, 2) 3), 3.50 (m, 1), 3.19 (bs, 1), 2.35 (t, 2), 1.85 (m, 1), 1.67 (m, 1), 1.49 (m, 2), 0.92 (t, 3).

Anal. Calcd. for C$_{14}$H$_{21}$NO$_3$: C, 66.91; H, 8.42; N, 5.57. Found: C, 67.26; H, 8.71; N, 5.55.

EXAMPLE 2

6-(4-Methoxybenzylamino)hexan-3-ol (3.0.0)

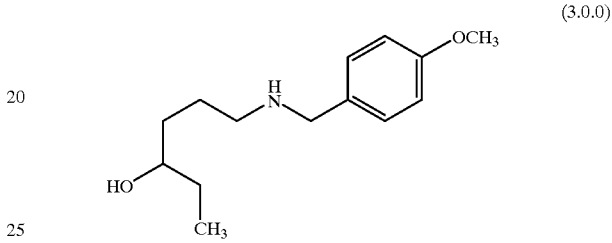

(3.0.0)

Tetrahydrofuran (121 gal, 458 L) and sodium borohydride (22.154 kg, 585.6 moles) were charged to a clean and dry nitrogen purged 500 gallon glass lined tank. The suspension was allowed to stir for 30 minutes at 20–25° C. then 4-hydroxyhexanoic acid 4-methoxy-benzylamide (45.75 kg, 182 moles) was added as a solid. After 30 minutes, the reaction was cooled to 5–10° C. and over a 4 to 8 hour period a solution of acetic acid (9.1 gallons, 34.4 L) in tetrahydrofuran (12 gal, 45.4 L) was added keeping the temperature at 0–10° C. A slight nitrogen bleed was kept on the tank to help remove the hydrogen. When the addition was complete the reaction was warmed to 20–25° C. and stirred for an hour. The temperature of the reaction was slowly increased to a gentle reflux (~66° C.) and held there for 16 hours. The reaction was quenched by the addition of 1N HCl, keeping the temperature <25° C. Excess tetrahydrofuran was removed by atmospheric distillation. Ethyl acetate was added to the resulting aqueous solution to extract unreacted amide. The acidic aqueous was then brought to pH 11 to allow the product amine to be extracted into ethyl acetate and held for use in the next step. An aliquot of the ethyl acetate solution of product was worked up to project final yield and concentration. The yield for this large scale run was 55.0%, which was less than that achieved with small scale preparations (78.8%). The large scale procedure had 12.8% unreduced amide starting material after the quench which accounted in part for the lower yield.

$^1$HMR (CDCl3, 300 MHz) δ7.21 (d, 2), 6.83 (d, 2), 3.78 (s, 3), 3.69 (s, 2), 3.41 (m, 2), 2.78 (m, 1), 2.58 (m, 1), 1.71 (m, 2), 1.45 (m, 4), 0.95 (t, 3). GC mass spectrum: m/e, 237. (M$^+$).

EXAMPLE 3
N-(4-Hydroxyhexyl)-N-(4-methoxybenzyl)oxalamic acid ethyl ester (4.0.0)

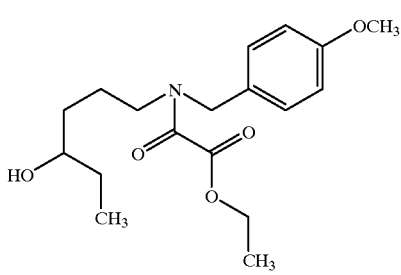

(4.0.0)

6-(4-Methoxybenzylamino)hexan-3-ol (24 kg, 101.1 moles) in ethyl acetate (158 gal, 598 L) was charged to a clean and dry, nitrogen purged 500 gallon tank. This solution was cooled to 0–5° C., then a solution of sodium bicarbonate (16.988 Kg, 202.2 moles in 51 gal (193 L) of water) was added, maintaining a temperature of 0° to 5° C. A solution of ethyl oxalyl chloride (16.566 Kg, 121.4 moles) in ethyl acetate (20 gal, 75.7 L) was added while maintaining a temperature of 0–5° C. over a time period of about 25 minutes. The reaction was allowed to warm to 20–25° C. at which point it was complete by HPLC. The reaction was stirred for an additional 16 hours to allow any residual ethyl oxalyl chloride to decompose. The lower aqueous layer was disposed of and the ethyl acetate was washed with 49 gal (185.5 L) of water. The layers were separated. The remaining ethyl acetate was washed with a solution of 2 N HCl (5.6 gal (21.2 L) of concentrated HCl plus 28.4 gal, (107.5 L) of water). The remaining ethyl acetate was vacuum stripped to obtain the crude product amide as an oil, 29.296 kg (85.9% theory).

[1]HMR (CDCl3, 400 MHz) δ7.18 (m, 2), 6.83 (m, 2), 4.41 (m, 1), 4.31 (m, 3), 3.76 (d, 3), 3.43 (m, 1), 3.25 (m, 1), 3.13 (t, 1), 2.00 (bs, 1), 1.80–1.26 (m, 8), 0.87 (t, 3). IR (neat) 3456, 1739, 1654, 1513 cm$^{-1}$ CMR (CDCl$_3$, 100 MHz) δ163.5, 162.1, 159.7, 159.0, 129.6, 129.2, 128.0, 127.1, 114.2, 114.1, 72.6, 72.5, 62.1, 55.3, 50.9, 47.0, 46.3, 43.6, 33.5, 33.4, 30.3, 30.2, 24.3, 22.9, 14.0, 9.9. GC mass spectrum: m/e, 337 (M$^+$).

EXAMPLE 4
N-(4-Methoxybenzyl)-N-(4-oxo-hexyl)oxalamic acid ethyl ester (5.0.0)

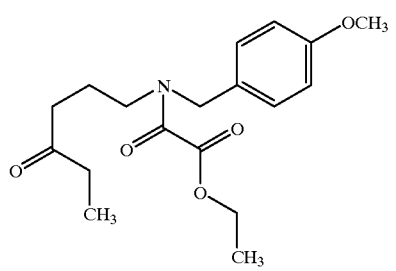

(5.0.0)

Potassium bromide (593 g, 5 moles) was dissolved in water (5 gal, 18.9 L) in a 100 gallon tank. A solution of oxalamide alcohol (33.62 Kg, 99.6 moles) in methylene chloride (34 gal, 128.7 L) was added. The 2,2,6,6-tetramethyl-1-piperidinyloxy (TEMPO) free radical catalyst (150 g) was added and the reaction cooled to 0–5° C. Fresh sodium hypochlorite solution (prepared from calcium hypochlorite (12.11 kg) and sodium carbonate (17.96 kg) in water (100 gal, 378.5 L) adjusted to pH 9.5 with sodium bicarbonate (1.7 kg) and filtered to remove calcium carbonate) was added slowly keeping the temperature at 10–15° C. When the reaction had been completed, the layers were separated and the aqueous extracted with 8 gallons of additional methylene chloride. The combined organic layers were washed with a solution made up with concentrated HCl (5.4 L) and potassium iodide (331 g) in water (3.84 gal, 14.5 L). The organic layer was then washed with a solution of sodium thiosulfate (1197 g) in water (5.3 gal, 20 L). The methylene chloride was washed with 10 gal (37.85 L) of water and then stripped without vacuum to an oil. The oil was stripped further after being transferred to the 50 L reactor. A yield of 33.407 kg of product was obtained, but this material contained 15 wt % methylene chloride (by nmr). The corrected yield was 28.396 kg (85.0% of theoretical).

[1]HMR (CDCl$_3$, 300 MHz) 67 7.18 (dd, 2), 6.82 (dd, 2), 4.49 (s, 1), 4.27 (m, 3), 3.74 (d, 3), 3.22 (t, 1), 3.10 (t, 1), 2.34 (m, 4), 1.77 (m, 2), 1.29 (m, 3), 0.98 (t, 3). [13]CMR (CDCl$_3$, 100 MHz) δ163.2, 163.1, 162.3, 159.5, 159.2, 145.6, 129.7, 129.2, 127.96, 127.1, 114.2, 114.1, 112.1, 62.1, 55.2, 50.6, 46.1, 46.1, 42.7, 39.0, 38.1, 35.8, 21.5, 20.6, 13.9, 7.7. GC mass spectrum: mie, 335 (M$^+$).

EXAMPLE 5
3-Hydroxy-1-(4-methoxybenzyl)-4-propionyl-5,6-dihydro-1H-pyridin-2-one (6.0.0)

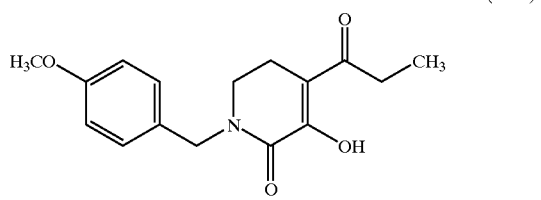

(6.0.0)

Oxalamide ketone (28.296 Kg, 84.4 moles) was dissolved in dry tetrahydrofuran (28 gal, 106 L) in a clean and dry 100 gallon tank. This solution was added to a solution of potassium t-butoxide (10.392 Kg) in tetrahydrofuran (42 gal, 159 L) in a 300 gallon tank over a 30 minute period keeping the temperature <35° C. After 1 hour at 20–25° C., the reaction was complete by HPLC. Water (98 gal, 371 L) was added to the reaction, followed by iso-propyl ether (24 gal, 90.8 L). The layers were separated and the aqueous containing the product as its potassium salt was washed a second time with iso-propyl ether. The aqueous was evaporated partially in vacuo to remove any residual THF and acidified to pH 2.1 by the addition of 6N HCl (4 gal, 15.1 L). The resulting slurry was filtered and the solids washed with water. The product was air dried at 50° C. to provide 17.9 kg of product (73%); mp 102–103° C.

[1]HMR (CDCl3, 300 MHz) 67 7.20 (d, 2), 6.86 (d, 2), 4.60 (s, 2), 3.70 (s, 3), 3.33 (t, 2), 2.69 (q, 2), 2.56 (t, 2), 1.13 (t, 3).

EXAMPLE 6
3-Methoxy-1-(4-methoxybenzyl)-4-propionyl-5,6-dihydro-1H-pyridin-2-one (7.0.0)

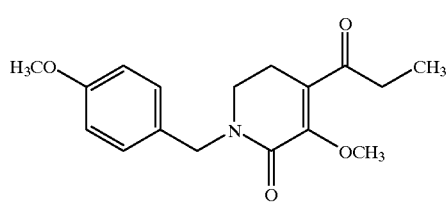

(7.0.0)

3-Hydroxy-1-(4-methoxybenzyl)-4-propionyl-5,6-dihydro-1H-pyridin-2-one (17.35 kg, 60 moles) and cesium carbonate (22.126 kg, 67.9 moles) were added to dry dimethylformamide (24 gal, 90.8 L) in a clean, dry 100 gallon tank. The suspension was stirred a half hour to insure dispersion. Dimethyl sulfate (8.552 kg, 67.8 moles) was added neat over a period of 30 minutes keeping the temperature 20–25° C. When the charge was complete the addition funnel was rinsed into the tank with additional DMF (500 ml). The reaction was allowed to stir at 20–25° C. for 16 hours. The reaction was diluted with ethyl acetate (108 gal, 408.8 L) and was washed with water (4×22 gal (83.3 L)). The ethyl acetate solution was washed with a solution made up of 6.94 liters 50% sodium hydroxide in 22 gal (83.3 L) of water followed by washing with a solution made up with 6.94 liters of concentrated HCl in 22 gal (83.3 L) of water. The organic solution was dried by washing with brine (14 gal, 53 L) The ethyl acetate was vacuum stripped to an oil which was suitable for use in the next step. The estimated yield based on NMR analysis of residual solvent was 89%. A small sample was isolated for characterization.
$^1$HMR (CDCl$_3$, 300 MHz) δ7.14 (d, 2), 6.78 (d, 2), 4.51 (s, 2), 3.88 (s, 3), 3.71 (s, 3), 3.2 (t, 2), 2.81 (q, 2), 2.42 (t, 2), 1.02 (t, 3). $^{13}$CMR (CDCl$_3$, 100 MHz) δ201.8, 159.1, 145.6, 129.3, 128.7, 126.5, 114.1, 60.2, 55.2, 49.6, 43.8, 37.0, 22.8, 8.1. GC mass spectrum: m/e, 303 (M$^+$).

EXAMPLE 7
Cyclopentylhydrazine dihydrochloride

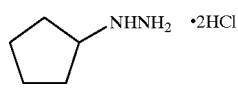

(7.1.0)

Cyclopentanol (6.127 kg, 71.1 moles) and triphenylphosphine (18.667 kg, 71.25 moles) were dissolved in tetrahydrofuran (40 gal) in a clean and dry, nitrogen purged 100 gallon tank and the reaction mixture was cooled to 5° C. A solution of di-t-butyl azodicarboxylate (14.9 kg, 64.7 moles) in tetrahydrofuran (36 L) was added over about 2 hours keeping the temperature <6° C. The reaction was allowed to stir for 5 hours as the temperature was allowed to slowly increase to 20–25° C. 6N HCl (26.5 L) was added to the reaction which was at 20° C. The reaction was allowed to stir 24 hours at 20–25° C. at which point the starting material had reacted. Water (10 gal, 37.85 L) was added and the tetrahydrofuran was removed by vacuum distillation. During the concentration, triphenylphosphine oxide precipitated and an additional 20 gal (75.7 L) of water was added. The reaction was cooled and methylene chloride (30 gal, 113.6 L) was added. The layers were separated and the aqueous was extracted twice more with methylene chloride (10 gal, 37.85 L) The aqueous was distilled to remove water. As the volume was reduced, isopropanol (3×20 gal (75.7 L)) was added to azeotrope the residual water. The resulting slurry was filtered and the solids were vacuum oven dried to give 7.682 kg (68.6% of theoretical) over multiple crops. This material was characterized to be the dihydrochloride salt; mp 189–194° C.
$^1$HMR (DMSO-d$_6$, 300 MHz) δ3.48 (m, 1), 1.79 (m, 2), 1.64 (m, 4), 1.49 (m, 2).

EXAMPLE 8
1-Cyclopentyl-3-ethyl-6-(4-methoxybenzyl)-1,4,5,6-tetrahydropyrazolo[3,4-c]pyridin-7-one

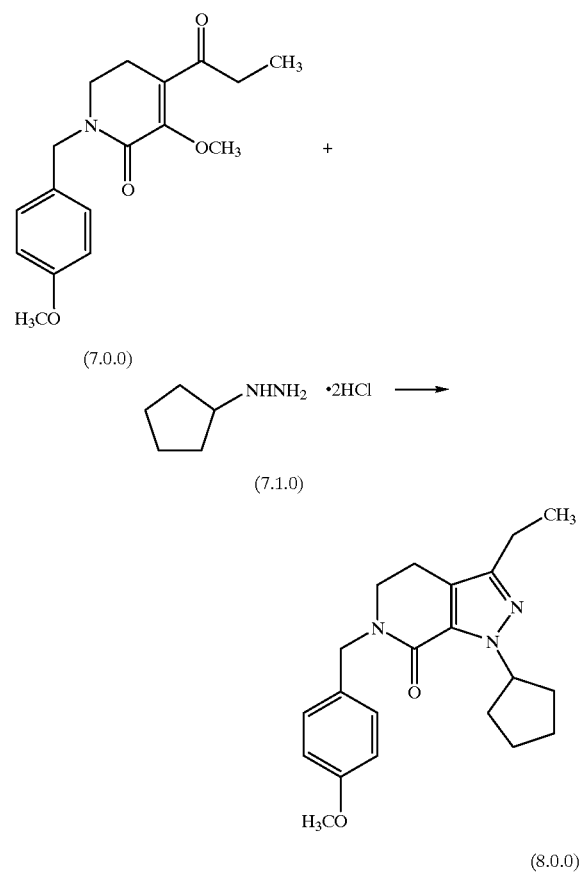

3-Methoxy-1-(4-methoxybenzyl)-4-propionyl-5,6-dihydro-1H-pyridin-2-one (14.471 kg, 47.76 moles) was dissolved in tetrahydrofuran (10.5 gal, 39.7 L) in a clean and dry 100 gallon tank. Cyclopentylhydrazine dihydrochloride (7.664 kg, 44.3 moles) was added and the reaction mixture warmed slowly to 88° C. while nitrogen was swept over the reaction to remove methanol, THF, and HCl. The reaction was monitored by HPLC until the conversion was complete which required heating overnight in most cases. The pot reaction product was a thick dark oil. A sample of 1-cyclopentyl-3-ethyl-6-(4-methoxybenzyl)-1,4,5,6-tetrahydropyrazolo[3,4-c]pyridin-7-one was isolated for characterization.
1HMR (CDCl$_3$, 300 MHz) 67 7.23 (d, 2), 6.85 (d, 2), 5.72 (m, 1), 4.62 (s, 2), 3.77 (s, 3), 3.44 (t, 2), 2.62 (t and q, 4), 2.06 (m, 4), 1.89 (m, 2), 1.67 (m, 2), 1.17 (t, 3). $^{13}$CMR (CDCl$_3$, 100 MHz) δ159.5, 159.0, 148.0, 145.6, 129.6, 129.3, 118.5, 114.0, 112.9, 60.4, 55.2, 48.6, 47.2, 32.7, 24.4, 20.2, 19.9, 13.8. GC mass spectrum: m/e, 353 (M$^+$). The product of this step could be used directly in the next step or purified as a p-toluenesulfonic acid or benzenesulfonic acid salt as described.

EXAMPLE 9

Preparation of the p-toluenesulfonic acid and benzenesulfonic acid salts of 1-cyclopentyl-3-ethyl-6-(4-methoxybenzyl)-1,4,5,6-tetrahydropyrazolo[3,4-c]pyridin-7-one The crude lactam (1g, 2.83 mmoles) was dissolved in ethyl acetate (5 ml) and treated with a solution of anhydrous p-toluenesulfonic acid (0.487 g, 2.83 mmoles) in ethyl acetate (2 ml). The salt crystallized from the mixture which was then cooled and filtered to provide 1.21 g of pure tosylate salt as a white solid in 81% yield; mp 110–113.8° C.

Anal. Calcd. for $C_{28}H_{35}N_3O_5S$: C, 63.98; H, 6.71; N, 7.99; S, 6.10. Found: C, 63.83; H, 6.69; N, 8.02; S, 6.14.

The benzenesulfonic acid salt was formed in the same manner; mp 126.6–131.4° C.

Anal. Calcd. for $C_{27}H_{33}N_3O_5S$: C, 63.38; H, 6.50; N, 8.21. Found: C, 63.09; H, 6.48; N, 8.21.

Either of these crystalline salts can be used in the deprotection reaction with trifluoroacetic acid and methanesulfonic acid described in the next example.

EXAMPLE 10

1-Cyclopentyl-3-ethyl-1,4,5,6-tetrahydropyrazolo[3,4-c]pyridin-7-one (9.0.0)

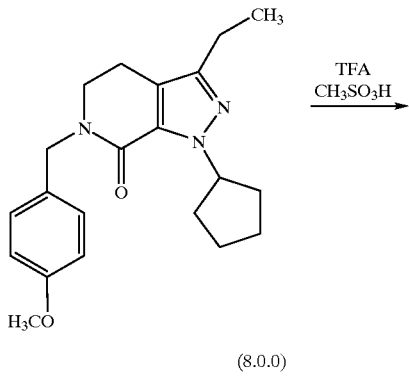

(8.0.0)

TFA
CH$_3$SO$_3$H
→

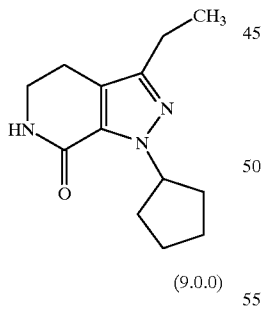

(9.0.0)

The reaction mixture from Example 8 was cooled to 55° C. and slowly thereto trifluoroacetic acid (87.3 kg, 764 moles) was added while keeping the temperature between 50–60° C. The first ⅓ of the charge was exothermic and required external cooling. Methanesulfonic acid (6342 ml, 97.7 moles) was added and the reaction was warmed to ~70° C. for two hours. The reaction was cooled to 20–25° C. and methylene chloride (17 gal, 64 L) was added followed by the slow addition of water (17 gal, 64 L). The layers were separated and the aqueous layer was diluted further with water (6 gal, 22.7 L) and then re-extracted with methylene chloride (6 gal, 22.7 L). The combined methylene chloride layers were mixed with water (29 gal, 110 L) and then brought to pH~7.0 by the addition of saturated sodium bicarbonate (ca. 45 gal, 170 L). The layers were separated and the methylene chloride atmospherically distilled to about 9 gal (35 L). Ethyl acetate (13 gal, 49 L) was added and the reaction mixture was distilled to about 9 gal (35 L). The resulting slurry was cooled and granulated. The solids were collected by filtration, washed with ethyl acetate and vacuum dried at 40° C. under full vacuum. The yield was 7.91 kg, 71.2%; mp 152–153° C.

$^1$HMR (CDCl$_3$, 300 MHz) δ5.61 (m, 2), 3.51 (dt, 2), 2.72 (t, 2), 2.62 (q, 2), 2.08 (m, 4), 1.90 (m, 2), 1.65 (m, 2), 1.40 (t, 3).

EXAMPLE 11

1-Cyclopentyl-7-ethoxy-3-ethyl-4,5-dihydro-1H-pyrazolo[3,4-c]pyridine (10.0.0)

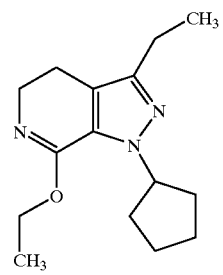

(10.0.0)

A solution of triethyloxonium tetrafluoroborate (3.371 kg, 17.74 moles) in methylene chloride (10.8 L) was slowly added to a suspension of 1-cyclopentyl-3-ethyl-1,4,5,6-tetrahydro-pyrazolo[3,4-c]pyridin-7-one (3.6 kg, 15.43 moles) in methylene chloride (7.2 L) over a period of about 40 minutes. The solution was then allowed to react for about 21 hours at 18–22° C. After the reaction was complete, the organic solution was washed with aqueous 10 % sodium carbonate (36 L) and evaporated to an oil which was used directly in the next step. The yield for this step was 92.9%.

$^1$HMR (CDCl$_3$, 300 MHz) δ5.14 (quintet, 1), 4.25 (q, 2), 3.62 (t, 2), 2.58 (m, 4), 2.07 (m, 4), 1.88 (m, 2), 1.61 (m, 2), 1.35 (t, 3), 1.19 (t, 3). GC mass spectrum: m/e, 261 (M$^+$).

EXAMPLE 12

8Cyclopentyl-6-ethyl-3-thiophen-2-yl-5,8-dihydro-4H-1,2,3a,7,8-pentaaza-as-indacene

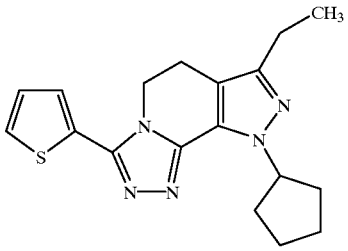

A solution of 1cyclopentyl-7-ethoxy-3-ethyl-4,5-dihydro-1H-pyrazolo[3,4-c]pyridine (3.739 kg, 14.3 moles) and 2thiophenecarboxylic hydrazide (2.237 kg, 15.8 moles) were heated in a solution in 1-butanol (37 L) to ~90° C. in a 50 gal tank for 48 hours. At this point, some 1-butanol was distilled off to remove water azeotropically. The reaction was concentrated to a low volume and 4 gallons of meth- 5ylene chloride (4 gal, 15 L) was added. The organics were washed twice with 1 N HCl (8 gal, 30.3 L) and concentrated by distillation to low volume. Isopropanol (16 L) was added to the concentrate and the resulting slurry was cooled and granulated. The product was collected by filtration and vacuum oven dried at 40° C. The yield was 3.25 kg (67%) of a white solid; mp 126° C.

$^1$HMR (CDCl$_3$, 300 MHz) δ7.51 (m, 2), 7.28 (s, 1), 7.20 (dd, 1), 5.61 (m, 1), 4.35 (t, 2), 3.00 (t, 2), 2.70 (q, 2), 2.18 (m, 4), 1.97 (m, 2), 1.62 (m, 2), 1.29 (t, 3).

Anal. Calcd. for $C_{18}H_{21}N_5S$: C, 63.69; H, 6.24; N, 20.63. Found: C, 63.82; H, 6.30; N, 20.77.

EXAMPLE 13
3tert-Butyl-8-cyclopentyl-6-ethyl-5,8-dihydro-4H-1,2,3a,7,8-pentaaza-as-indacene

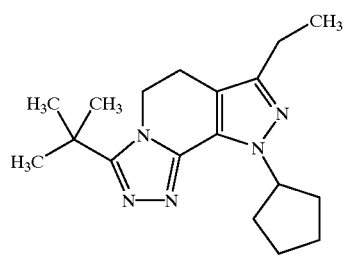

A solution of 1-cyclopentyl-7-ethoxy3-ethyl4,5-dihydro-1H-pyrazolo[3,4-c]pyridine (5 g, 19.4 mmoles) and 2,2-dimethylpropionic carboxylic hydrazide (2.48 g, 21.4 mmoles) was heated in a solution in 1-butanol (30 ml) to reflux for 48 hours. The solvent was evaporated at reduced pressure and the residual oil was dissolved in methylene chloride. The organic solution was washed with 1N HCl (50 ml) and dried over calcium chloride. The solution was filtered, evaporated in vacuo and the crude product was crystallized from isopropanol. The yield was 2.76 g (45%) of an off-white solid; mp 150–151° C.

$^1$HMR (CDCl$_3$, 300 MHz) δ5.50 (m, 1), 4.49 (t, 2), 3.15 (t, 2), 2.68 (q, 2), 2.13 (m, 4), 1.93 (m, 2), 1.70 (m, 2), 1.60 (s, 9), 1.24 (t, 3).

Anal. Calcd. for $C_{18}H_{27}N_5$: C, 68.97; H, 8.68; N, 22.34. Found: C, 69.05; H, 8.89; N, 22.46.

What is claimed is:

1. A method of preparing an 8-cyclopentyl-6-ethyl-3-[substituted]-5,8-dihydro-4H-1,2,3a,7,8-pentaaza-as-indacene compound of Formula (1.0.0):

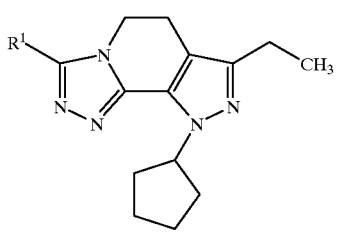

and pharmaceutically acceptable salt forms thereof, wherein:

$R^1$ is a member independently selected from the group consisting of hydrogen; ($C_1$–$C_6$) alkyl; ($C_1$–$C_4$) alkoxy; ($C_1$–$C_4$) alkoxy($C_1$–$C_4$) alkyl; ($C_2$–$C_8$) alkenyl; ($C_3$–$C_7$) cycloalkyl and 1'-methyl thereof; ($C_3$–$C_7$) cycloalkyl($C_1$–$C_2$) alkyl; a saturated or unsaturated ($C_4$–$C_7$) heterocyclic-(CH$_2$)$_n$— group where n is an integer selected from 0, 1, and 2, comprising one or two heteroatoms independently selected from O, S, S(=O)$_2$, N, NR$^3$, O together with N or NR$^3$, S or S(=O)$_2$ together with N or NR$^3$, and N or NR$^3$ together with N or NR$^3$; where:

$R^3$ is hydrogen or ($C_1$–$C_4$) alkyl; or $R^1$ is a group of Formula (1.1.0):

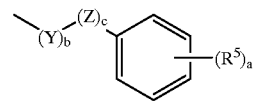

wherein:

a is an integer selected from 1 through 5, inclusive;

b and c are each independently an integer selected from 0 and 1;

$R^5$ is a member independently selected from the group consisting of hydrogen; hydroxy; ($C_1$–$C_4$) alkyl; ($C_2$–$C_4$) alkenyl; ($C_1$–$C_4$) alkoxy; ($C_3$–$C_6$) cycloalkoxy; halogen; trifluoromethyl; $CO_2R^{3a}$; $CONR^{3a}R^{3b}$; $NR^{3a}R^{3b}$; $NO_2$; and $SO_2NR^{3a}R^{3b}$; where $R^{3a}$ and $R^{3b}$ are each independently selected from the group consisting of hydrogen and ($C_1$–$C_4$) alkyl;

Z is O, S, S(=O)$_2$, C(=O), or NR$^3$; and

Y is —($C_1$–$C_4$) alkylene- or —($C_2$–$C_4$) alkenylene-, either of which is optionally mono-substituted by hydroxy; wherein:

each above-recited alkyl, alkenyl, cycloalkyl, alkoxyalkyl and heterocyclic group is substituted by 0 to 3 substituents comprising a member independently selected from group consisting of ($C_1$–$C_2$) alkyl, trifluoromethyl, and halogen; comprising:

(a) subjecting a solventless reaction mixture of γ-caprolactone and p-methoxybenzylamine to heating whereby there is produced an amide compound N-protected by p-methoxybenzyl, of Formula (2.0.0):

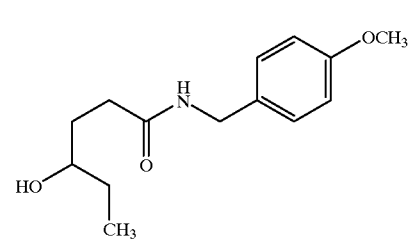

(b) reducing said amide compound of Formula (2.0.0) whereby there is produced an amino alcohol compound N-protected by p-methoxybenzyl, of Formula (3.0.0):

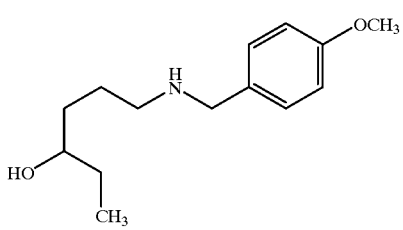
(3.0.0)

(c) acylating said aminoalcohol compound of Formula (3.0.0) with ethyl oxalyl chloride whereby there is produced an oxalamic acid ethyl ester compound N-protected by p-methoxybenzyl, of Formula (4.0.0):

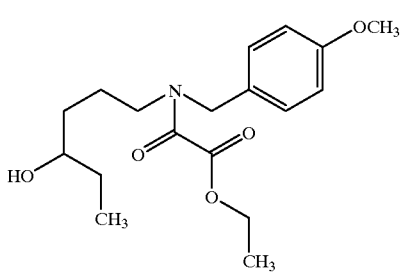
(4.0.0)

(e) oxidizing said oxalamic acid ethyl ester compound of Formula (4.0.0) whereby there is produced an oxalamide ketone compound N-protected by p-methoxybenzyl, of Formula (5.0.0):

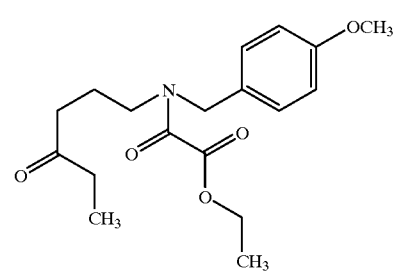
(5.0.0)

(e) ring closing said oxalamide ketone compound of Formula (5.0.0) whereby there is produced a pyridinone compound N-protected by p-methoxybenzyl, of Formula (6.0.0):

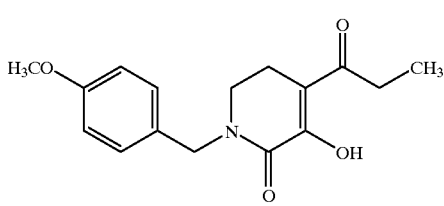
(6.0.0)

(f) O-methylating said pyridinone compound of Formula (6.0.0) whereby there is produced a 3-methoxy-pyridinone compound N-protected by p-methoxybenzyl, of Formula (7.0.0):

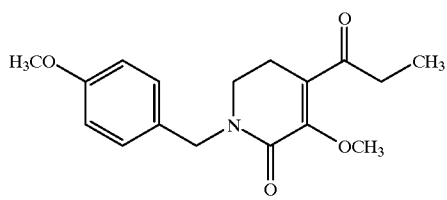
(7.0.0)

(g) treating said 3-methoxy-pyridinone compound of Formula (7.0.0) with cyclopentylhydrazine, whereby there is produced a pyrazolopyridinone compound N-protected by p-methoxybenzyl, of Formula (8.0.0):

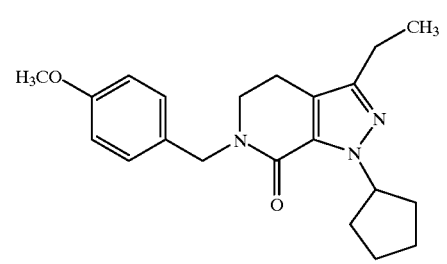
(8.0.0)

(h) deprotecting said pyrazolopyridinone compound of Formula (8.0.0) by removing said p-methoxybenzyl group therefrom, whereby there is produced a lactam compound of Formula (9.0.0):

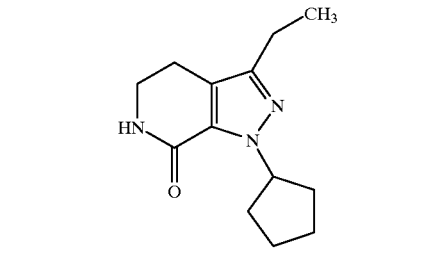
(9.0.0)

(i) esterifying said lactam compound of Formula (9.0.0) whereby there is produced a corresponding imino ester (imidate) compound of Formula (10.0.0):

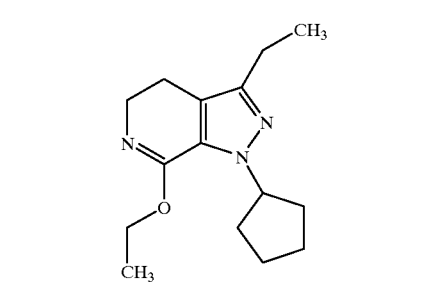
(10.0.0)

(j) treating said imino ester (imidate) compound of Formula (10.0.0) with a carboxylic hydrazide compound of Formula (11.0.0):

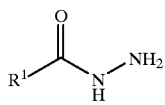

where R¹ has the same meaning as set out further above; whereby there is produced said 8-cyclopentyl-6-ethyl-3-[substituted]-5,8-dihydro-4H-1,2,3a,7,8-pentaaza-as-indacene compound of Formula (1.0.0).

2. A method according to claim 1 wherein in Step (j) for said carboxylic hydrazide compound of Formula (11.0.0):

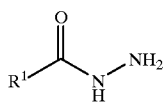

$R^1$ is 2-thiophene or tert-butyl; wherein a reaction mixture is established with a solution of said compound of Formula (9.0.0) in 1-butanol, and of 2-thiophenecarboxylic hydrazide, or alternatively, of 2,2-dimethylpropionic carboxylic hydrazide; and wherein said reaction mixture is heated at a temperature of from 85° to 95° C., preferably 90° C. over a period of from 36 to 60 hours, preferably 48 hours.

3. A method according to claim 2 wherein said reaction mixture is heated at a temperature of 90° C. over a period of 48 hours.

4. A method according to claim 2 wherein there is produced 8-cyclopentyl-6-ethyl-3-thiophen-2-yl-5,8-dihydro-4H-1,2,3a,7,8-pentaaza-as-indacene of Formula (1.0.1), and 8-cyclopentyl-6-ethyl-3-t-butyl-5,8-dihydro-4H-1,2,3a,7,8-pentaaza-as-indacene of Formula (1.0.2):

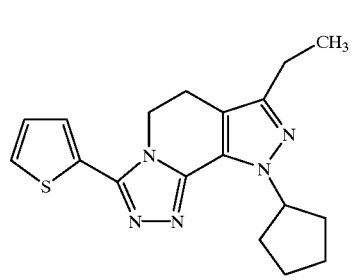

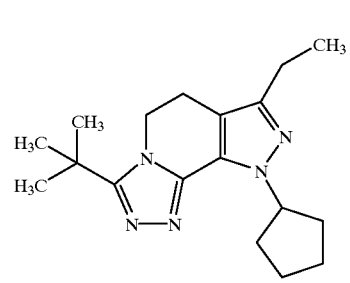

5. A method of preparing an 8-cyclopentyl-6-ethyl-3-[substituted]-5,8-dihydro-4H-1,2,3a,7,8-pentaaza-as-indacene compound of Formula (1.0.0):

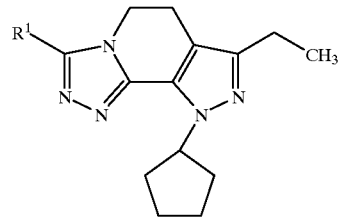

and pharmaceutically acceptable salt forms thereof, wherein:

$R^1$ is a member independently selected from the group consisting of hydrogen; $(C_1-C_6)$ alkyl; $(C_1-C_4)$ alkoxy; $(C_1-C_4)$ alkoxy$(C_1-C_4)$ alkyl; $(C_2-C_8)$ alkenyl; $(C_3-C_7)$ cycoloalkyl and 1'-methyl thereof; $(C_3-C_7)$ cycloalkyl$(C_1-C_2)$ alkyl; a saturated or unsaturated $(C_4-C_7)$ heterocyclic-$(CH_2)_n$— group where n is an integer selected from 0, 1, and 2, comprising one or two heteroatoms independently selected from O, S, $S(=O)_2$, N, $NR^3$, O together with N or $NR^3$, S or $S(=O)_2$ together with N or $NR^3$, and N or $NR^3$ together with N or $NR^3$; where:

$R^3$ is hydrogen or $(C_1-C_4)$ alkyl; or $R^1$ is a group of Formula (1.1.0):

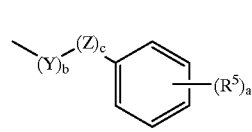

wherein:
a is an integer selected from 1 through 5, inclusive;
b and c are each independently an integer selected from 0 and 1;
$R^5$ is a member independently selected from the group consisting of hydrogen; hydroxy; $(C_1C_4)$ alkyl; $(C_2-C_4)$ alkenyl; $(C_1-C_4)$ alkoxy; $(C_3-C_6)$ cycloalkoxy; halogen; trifluoromethyl; $CO_2R^{3a}$; $CONF^{3a}R^{3b}$; $NR^{3a}R^{3b}$; $NO_2$; and $SO_2NR^{3a}R^{3b}$; where
$R^{3a}$ and $R^{3b}$ are each independently selected from the group consisting of hydrogen and $(C_1-C_4)$ alkyl;
Z is O, S, $S(=O)_2$, $C(=O)$, or $NR^3$; and
Y is —$(C_1-C_4)$ alkylene- or —$(C_2-C_4)$ alkenylene-, either of which is optionally mono-substituted by hydroxy; wherein:
each above-recited alkyl, alkenyl, cycloalkyl, alkoxy-alkyl and heterocyclic group is substituted by 0 to 3 substituents comprising a member independently selected from group consisting of $(C_1-C_2)$ alkyl, trifluoromethyl, and halogen; comprising:

(a) subjecting a solventless reaction mixture of γ-caprolactone and p-methoxybenzylamine to heating to a temperature in the range of from 80° to 85° C. for 16 hours, whereby there is produced an amide compound N-protected by p-methoxybenzyl, of Formula (2.0.0):

(2.0.0)

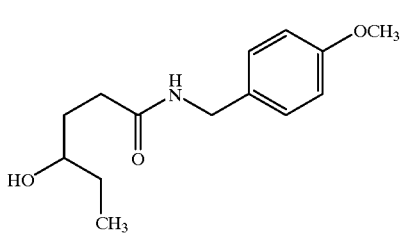

(b) reducing said amide compound of Formula (2.0.0) using as a reducing agent sodium borohydride, NaBH₄; in conjunction with a proton source comprising acetic acid or tetrahydrofuran (THF) solution of said acetic acid; both together in a solvent consisting of tetrahydrofuran, THF; wherein after said sodium borohydride is added to said THF, said amide of Formula (2.0.0) is added as a solid to said reaction mixture which is thereafter cooled; said acetic acid in THF is added to said reaction mixture, which is then heated to a gentle reflux temperature in the range of 60° to 70° C. for a period of 16 hours; hydrogen gas is removed as a byproduct and unreacted amide is removed by extraction with ethyl acetate, after addition of 1N HCl in order to decompose excess reagent; and thereafter the pH of said reaction mixture is raised to 11 in order to permit the product of Formula (3.0.0) to be extracted into ethyl acetate and held for use in the next step; whereby there is produced an amino alcohol compound N-protected by p-methoxybenzyl, of Formula (3.0.0):

(3.0.0)

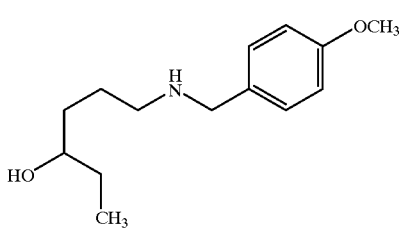

(c) acylating said amino alcohol compound of Formula (3.0.0) with ethyl oxalyl chloride as a solution in ethyl acetate, in accordance with Schotten-Baumann reaction conditions for treating an aqueous solution of sodium bicarbonate; wherein the reaction which takes place is exothermic, whereupon said ethyl oxalyl chloride is added over from 20 to 30 minutes, and said reaction temperature is maintained at 0° to 5° C. until said reaction is complete in from 1 to 2 hours; thereafter said reaction mixture is stirred at from 20° to 25° C. for 16 hours to permit unreacted ethyl oxalyl chloride to be removed by decomposition; whereby there is produced an oxalamic acid ethyl ester compound N-protected by p-methoxybenzyl, of Formula (4.0.0):

(4.0.0)

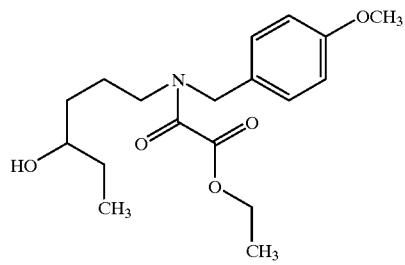

(d) oxidizing said oxalamic acid ethyl ester compound of Formula (4.0.0) using sodium hypochlorite oxidizing agent in the presence of the catalyst 2,2,6,6-tetramethyl-1-piperidinyloxy, free radical (TEMPO), wherein said sodium hypochlorite solution is made fresh when carrying out said oxidizing, comprising: dissolving calcium hypochlorite and sodium carbonate in water and adjusting the pH of the resulting solution to 9.5 with sodium bicarbonate, followed by filtering of said solution to remove remaining calcium carbonate side product in said solution; and further wherein a reaction mixture is established as a solution of said compound of Formula (4.0.0) in methylene chloride, CH₂Cl₂; in addition to potassium bromide, KBr, dissolved in water; to which said TEMPO catalyst is added and said reaction mixture is cooled to a temperature of from 0° to 5° C.; after which said sodium hypochlorite oxidizing agent is slowly added while said reaction mixture is maintained at a temperature of from 10° to 15° C.; whereby there is produced an oxalamide ketone compound N-protected by p-methoxybenzyl, of Formula (5.0.0):

(5.0.0)

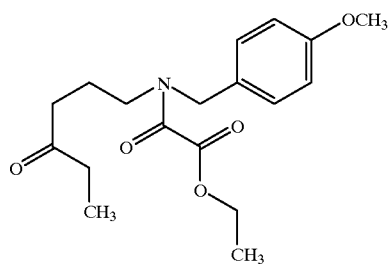

(e) ring closing said oxalamide ketone compound of Formula (5.0.0) under Dieckmann condensation reaction conditions, wherein a reaction is carried out in the presence of a relatively strong base consisting of potassium teit-butoxide, in tetrahydrofuran, di-iso-propyl ether, methyl tert-butyl ether, or toluene; wherein said base is added gradually over a period of 30 minutes, while said reaction mixture temperature is kept below 35° C., and said reaction proceeds to completion in 1.0 hour with said reaction mixture being at from 20° to 25° C.; whereby there is produced a pyridinone compound N-protected by p-methoxybenzyl, of Formula (6.0.0):

(6.0.0)

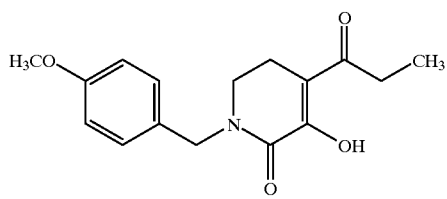

(f) O-methylating said pyridinone compound of Formula (6.0.0) by methylation with dimethylsulfate; wherein a reaction mixture is established with dimethylformamide (DMF) solvent in the presence of cesium carbonate, $Cs_2CO_3$, with gradual addition of said dimethylsulfate over a period of 30 minutes, while said reaction mixture temperature is kept at from 20° to 25° C.; and thereafter, said reaction mixture is maintained at said temperature and stirred for 16 hours; whereby there is produced a 3-methoxy-pyridinone compound N-protected by p-methoxybenzyl, of Formula (7.0.0):

(7.0.0)

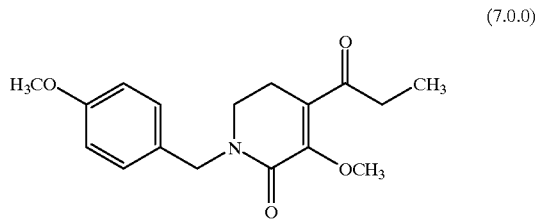

(g) treating said 3-methoxy-pyridinone compound of Formula (7.0.0) with cyclopentylhydrazine dihydrochloride; wherein a reaction mixture is established with tetrahydrofuran (THF) solvent and heating of said reaction mixture to 88° C., for 12 hours, while said reaction mixture is being swept by nitrogen in order to remove methanol, THF, and HCl; whereby there is produced a pyrazolopyridinone compound N-protected by p-methoxybenzyl, of Formula (8.0.0):

(8.0.0)

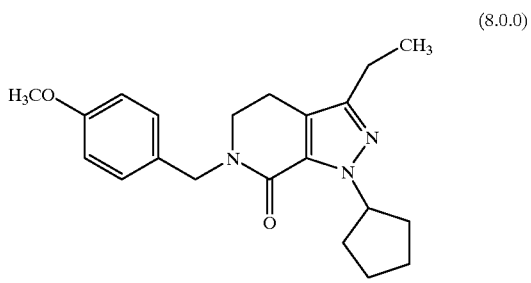

wherein said compound of Formula (8.0.0) may be used in the next step of the process without further treatment, or alternatively, may be purified as a p-toluenesulfonic acid or benzenesulfonic acid salt by dissolving said compound of Formula (8.0.0) in ethyl acetate and thereafter treating it with anhydrous p-toluenesulfonic acid dissolved in ethyl acetate or anhydrous benzenesulfonic acid dissolved in ethyl acetate; whereupon the respective salt crystallizes from the reaction mixture thus formed, which is then cooled and filtered to provide the pure p-toluenesulfonate (tosylate) or benzenesulfonate (besylate) salt;

(h) deprotecting said pyrazolopyridinone compound of Formula (8.0.0) by removing said p-methoxybenzyl group therefrom; wherein a reaction mixture is established at a temperature of 55° C.; after which trifluoroacetic acid (TFA) is added slowly, the initial addition of TFA causing exothermic reaction conditions which require external cooling; thereafter methanesulfonic acid, $CH_3SO_3H$, is added to said reaction mixture, the temperature of which is raised to 70° C., at which temperature said reaction mixture is maintained for 2 hours; and thereafter said reaction mixture is cooled to a temperature of from 20° to 25° C.; whereby there is produced a lactam compound of Formula (9.0.0):

(9.0.0)

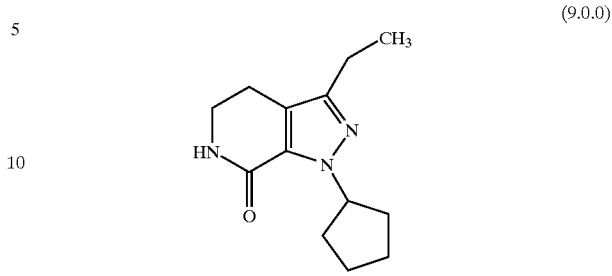

(i) esterifying said lactam compound of Formula (9.0.0) using triethyloxonium tetrafluoroborate, $(CH_3CH_2)_2OBF_4$; wherein a reaction mixture is established by slowly adding a solution of triethyloxonium tetrafluoroborate, $(CH_3CH_2)_3OBF_4$ in methylene chloride to a suspension of said lactam compound of Formula (9.0.0) in methylene chloride over a period of 40 minutes; and thereafter, maintaining said reaction mixture at a temperature of from 18° to 22° C., for a period of 21 hours; whereby there is produced a corresponding imino ester (imidate) compound of Formula (10.0.0):

(10.0.0)

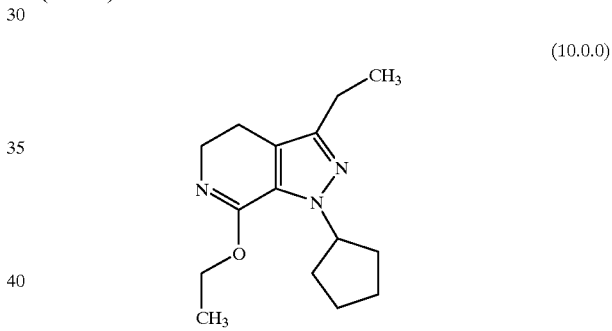

(j) treating said imino ester (imidate) compound of Formula (10.0.0) with a carboxylic hydrazide compound of Formula (11.0.0):

(11.0.0)

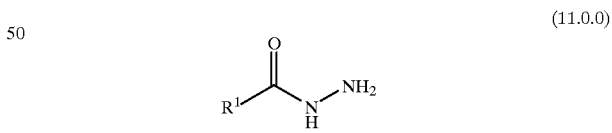

where $R^1$ is 2-thiophene or tert-butyl; wherein a reaction mixture is established with a solution of said compound of Formula (9.0.0) in 1-butanol, and of 2-thiophenecarboxylic hydrazide, or alternatively, of 2,2-dimethylpropionic carboxylic hydrazide; and said reaction mixture is heated at a temperature of 90° C. over a period of 48 hours; whereby there is produced 8-cyclopentyl-6-ethyl-3-thiophen-2-yl-5,8-dihydro-4H-1,2,3a,7,8-pentaaza-as-indacene of Formula (1.0.1), and 8-cyclopentyl-6-ethyl-3-t-butyl-5,8-dihydro-4H-1,2,3a,7,8-pentaaza-as-indacene of Formula (1.0.2):

(1.0.1)

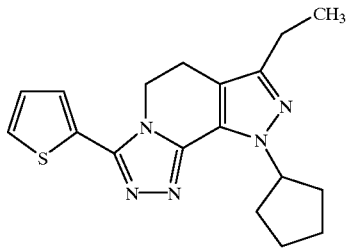

(1.0.2)

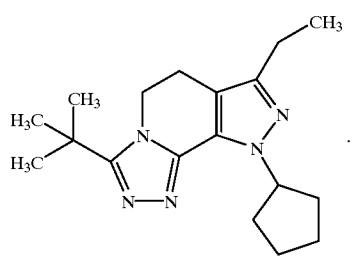

6. An improved method of preparing an 8-cyclopentyl-6-3-[substituted]-5,8-dihydro-4H-1,2,3a,7,8-pentaaza-as-indacene compound of Formula (1.0.0):

(1.0.0)

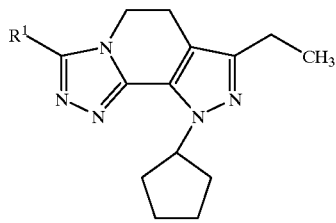

and pharmaceutically acceptable salt forms thereof, wherein $R^1$ is as defined in claim 1; comprising:

(a) esterifying a lactam compound of Formula (9.0.0):

(9.0.0)

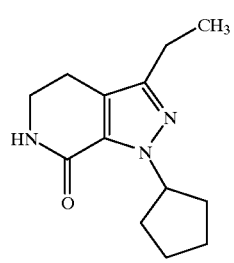

whereby there is produced a corresponding imino ester (imidate) compound of Formula (10.0.0):

(10.0.0)

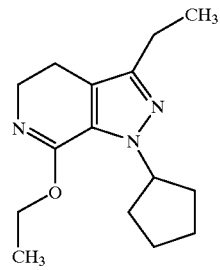

(b) treating said imino ester (imidate) compound of Formula (10.0.0) with a carboxylic hydrazide compound of Formula (11.0.0):

(11.0.0)

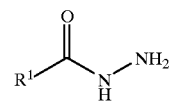

where $R^1$ is as defined in claim 1; whereby there is produced said 8-cyclopentyl-6-ethyl-3-[substituted]-5,8-dihydro-4H-1,2,3a,7,8-pentaaza-as-indacene compound of Formula (1.0.0).

7. An improved method of preparing an 8-cyclopentyl-6-ethyl-3-[substituted]-5,8-dihydro-4H-1,2,3a,7,8-pentaaza-as-indacene compound of Formula (1.0.0):

(1.0.0)

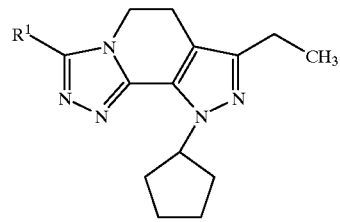

and pharmaceutically acceptable salt forms thereof, wherein $R^1$ is as defined in claim 1, comprising:

treating an imino ester (imidate) compound of Formula (10.0.0):

(10.0.0)

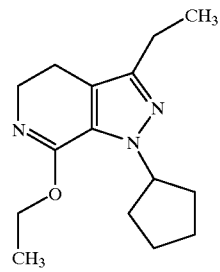

with a carboxylic hydrazide compound of Formula (11.0.0):

(11.0.0)
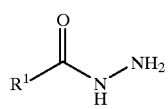
where R¹ is as defined in claim 1; whereby there is produced said 8-cyclopentyl-6-ethyl-3-[substituted]-5,8-dihydro-4H-1,2,3a,7,8-pentaaza-as-indacene compound of Formula (1.0.0).
8. An imino ester (imidate) of Formula (10.0.0):
(10.0.0)
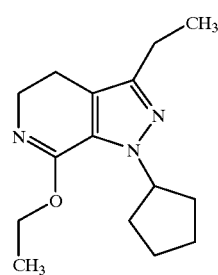
and pharmaceutically acceptable salt forms thereof.
9. A compound according to claim 8 selected from the tosylate and besylate salts thereof, of Formulas (10.1.0) and (10.2.0) as follows:
(10.1.0)
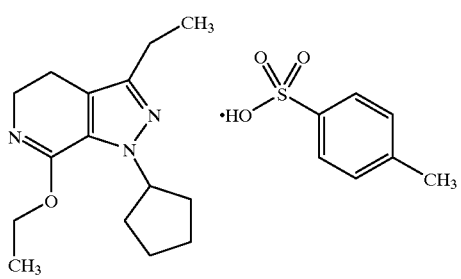
(10.2.0)
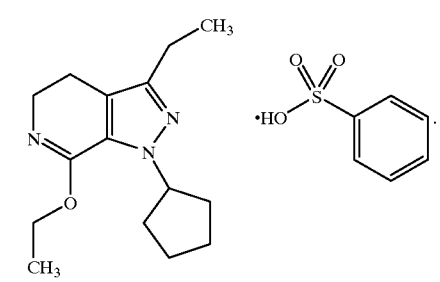
* * * * *